(12) United States Patent
Suzuki et al.

(10) Patent No.: US 6,790,798 B1
(45) Date of Patent: Sep. 14, 2004

(54) HIGHLY WATER ABSORBENT SHEET

(75) Inventors: Migaku Suzuki, Kamakura (JP); Ryoichi Matsumoto, Kunitachi (JP)

(73) Assignee: Japan Absorbent Technology Institute, Tokyo (JP)

( * ) Notice: Subject to any disclaimer, the term of this patent is extended or adjusted under 35 U.S.C. 154(b) by 310 days.

(21) Appl. No.: 09/667,815

(22) Filed: Sep. 22, 2000

(30) Foreign Application Priority Data

Sep. 29, 1999 (JP) ............................................ 11-276722

(51) Int. Cl.[7] .............................. B32B 5/18; B32B 5/24
(52) U.S. Cl. ...................................... 442/374; 442/373
(58) Field of Search ................................ 442/373, 374; 608/378, 385.01

(56) References Cited

U.S. PATENT DOCUMENTS

| | | | |
|---|---|---|---|
| 4,189,336 A | 2/1980 | Hutflesz | 156/72 |
| 5,217,798 A | * 6/1993 | Brady et al. | 442/381 |
| 5,679,042 A | 10/1997 | Varona | 442/347 |
| 5,821,179 A | 10/1998 | Masaki et al. | 442/375 |

FOREIGN PATENT DOCUMENTS

| | | |
|---|---|---|
| EP | 0 203 289 | 12/1986 |
| EP | 95/03019 | 2/1995 |
| EP | 97/04955 | 2/1997 |
| EP | 0 826 349 | 3/1998 |
| EP | 0 829 245 | 3/1998 |
| EP | 0 841 156 | 5/1998 |
| EP | 947549 | * 10/1999 |
| JP | 2000-201975 | 7/2000 |
| JP | 2000-238161 | 9/2000 |
| WO | 98/25999 | 6/1998 |
| WO | 00/47153 | 8/2000 |

* cited by examiner

Primary Examiner—Arden B Sperty
(74) Attorney, Agent, or Firm—Manabu Kanesaka

(57) ABSTRACT

A highly absorbent composite sheet wherein a non-woven substrate having a bulky structure and solid SAP with a part contained inside said bulky structure and the rest exposed on the surface of said non-woven substrate are provided, a thermally fusible component being a hot-melt adhesive, the hot-melt adhesive forming a fibrous network and covering said solid SAP and fine cellulose fibers in contact with the solid SAP whereby a single or double fibrous network is provided with the solid SAP held in position. A method for manufacturing same, and an absorbent article using such highly absorbent composite sheet are also provided.

11 Claims, 18 Drawing Sheets

|  | CASE 1 | CASE 2 | CASE 3 |
|---|---|---|---|
| 1st STEP HOTMELT PATTERN | <COARSE/DENSE CURTAIN SPRAY> | <COARSE/DENSE CURTAIN SPRAY> | <LINE COAT> |
| 2nd STEP HOTMETL PATTERN | <THICK- COARSE CURTAIN SPRAY> | <SPIRAL COAT> | <COARSE/DENSE CURTAIN SPRAY> |
| COVERED CONDITION OF THE SURFACE OF HIGHLY ABSORBENT SHEET | <COMBINATION OF CURTAIN SPRAY> | <COMBINATION OF CURTAIN SPRAY AND SPIRAL COAT> | <COMBINATION OF LINE COAT AND CURTAIN SPRAY> |

FIG. 11

HIGHLY WATER ABSORBENT SHEET

BACKGROUND OF THE INVENTION

1. Field of Art

The present invention relates to a highly water absorbing composite sheet and in particular, a highly water absorbing composite sheet with a highly water absorbing solid resin held in a non-woven substrate sheet and to a method of manufacturing the same. The present invention also relates to absorbent products using such highly water absorbing composite sheet.

In the present invention every shape of solid substances including particles, pellets, film or non-woven fabric like shape can be used as the highly water absorbing resin. In this specification, the term "highly water absorbing solid resin" or "solid SAP" is used to mean highly water absorbing resins of every such shape.

2. Related Art

Highly water absorbing composite sheet comprising a non-woven substrate sheet and solid SAP held on the surface of the non-woven substrate sheet has been used as an absorbent component in such absorbent products such as baby diapers, adult diapers, sanitary napkins, blood absorbent and mother's milk pads. Such highly water absorbing composite sheet is described in several patents such as U.S. Pat. No. 5,147,343.

Until now, in this type of highly water absorbing composite sheet, the fixing of solid SAP to a non-woven substrate sheet has been done by means of adhesiveness of a hot-melt adhesive. Or a method has been applied of coating the non-woven substrate sheet with a suspension of the solid SAP or a suspension of a mixture of the solid SAP and pulp. In the case of the solid SAP and pulp mixture system, the fixing of the solid SAP to the non-woven substrate sheet depends on the self-adhesiveness of the pulp.

In case a suspension containing the solid SAP is used, a suspension may sometimes be used where easy-to-thermally-melt binder fibers (for example, bicomponent fibers) are added. This suspension is applied on the non-woven substrate sheet and heated and then cooled down whereby the solid SAP and the pulp, if any, are fixed into the non-woven substrate sheet by means of the easy-to-thermally-melt binder fibers.

Another method of fixing the solid SAP into the non-woven substrate sheet is that easy-to-thermally-melt fibers or fiber web containing such easy-to-thermally-melt fibers are made to contain solid SAP and by means of heat treatment the fibers constituting such fiber web are fused together with the result that the solid SAP is fixed into the substrate.

In the conventional technology, however, in the case of the solid SAP and pulp mixture system in particular, it is difficult to increase the ratio of solid SAP/pulp ("SAP ratio") to a great extent and thus the maximum ratio has been around 50% by weight. In the system where the solid SAP is fixed by means of the binder, the swelling capacity of the solid SAP and the binding capacity of the solid SAP by means of the binder work in antagonistic action with each other. That is to say, the higher the binding capacity of the solid SAP, the more the swelling of the solid SAP is impeded and inversely if the swelling is less impeded, the binding of the solid SAP becomes more difficult.

Therefore, a primary object of the present invention is to provide a structure where as the solid SAP swells the substrate at the same time swells; that is to say, a structure where while the solid SAP and the substrate are so loosely bonded with each other as for the solid SAP to maintain its degree of freedom, the swollen solid SAP is so contained by the substrate that the solid SAP does not go away from the substrate.

SUMMARY OF THE INVENTION

According to the present invention, a highly absorbent composite sheet is provided comprising a non-woven fabric substrate, solid SAP and a thermally fusible component, characterized in that:

said non-woven substrate has a bulky structure;

part of said solid SAP is contained inside said bulky structure and the rest is exposed on the surface of said non-woven substrate;

said thermally fusible component is a hot-melt adhesive;

said hot-melt adhesive forms a fibrous network; and said fibrous network covers said solid SAP in contact with said solid SAP whereby said solid SAP is held in position.

The preferred range of the coated amount of said hot-melt adhesive is 0.2 to 10 $g/m^2$.

The hot-melt adhesive is preferably of non-tacking type; for example, an adhesive comprising as a main component a copolymer of ethylene and vinyl acetate is most preferable. The content of vinyl acetate in the ethylene /vinyl acetate copolymer is preferably 20 to 40% by weight and its thermal fluid coefficient is preferably 50 to 150 g/10 min.

According to the present invention, a method for manufacturing a highly absorbent composite sheet is provided comprising the steps of:

forming a bulky structure by raising a non-woven substrate;

applying slurry containing solid SAP to the raised surface of said non-woven substrate, then removing remaining liquid and drying whereby a part of solid SAP is contained in said bulky structure and the rest of solid SAP is exposed on the surface of said non-woven substrate; and making a hot-melt adhesive fibrous by means of a curtain spray apparatus, then blowing the adhesive in the form of a curtain and forming a fibrous network on said non-woven substrate and said solid SAP.

Raising can be made in a variety of manners. A preferable way of raising is to make one surface of a non-woven substrate in contact with a heated roll and then to make it in contact with a chilled roll after it is removed from the heated roll.

All solid SAP is preferably contained by the bulky structure of said non-woven substrate, i.e. in voids between and among the fibers constituting the non-woven substrate. Although, depending on the amount of solid SAP added and on the bulkiness of a carded web used, part of the solid SAP may be exposed on the non-woven substrate, it does not get in the way of achieving the object of the present invention.

Such exposed solid SAP, however, may turn into dust and particles as abraded or bent when the non-woven substrate containing the solid SAP is slit or it is incorporated into a product although such solid SAP appears to be stable as it is left stationary even if it is in dry condition. And such exposed solid SAP may easily be separated from the composite when it is swollen in wet condition. For stabilizing the solid SAP in such dry and wet conditions only by virtue of the containing capability of the non-woven substrate, preferably, the non-woven substrate needs to be made more bulky and the solid SAP to be contained by the substrate needs to be less. In other words, generally speaking, the non-woven substrate alone can hardly contain 70% or more of solid SAP used and the added amount of solid SAP can hardly be more than 300 g/m².

By utilizing a fibrous network based on the use of a hot-melt adhesive according to the present invention, such non-woven substrate as has not been so far used for being very often peeled off, for example, a spunbond (generally called "SB") or a composite of a spunbond/meltblown/ spunbond (generally called "SMS") is made usable as an absorbent substrate.

According to the another aspect of the present invention, there is provided a highly absorbent composite comprising a composite absorbent (M) which comprises a non-woven substrate, a SAP layer and a hot-melt adhesive layer forming a fibrous network covering said SAP layer, and a sheet material (N) disposed on said adhesive layer, said composite absorbent (M) and said sheet material (N) being bonded together by said hot-melt adhesive layer by an adhesive property thereof to form a composite structure (M/N).

In place of the sheet material (N), it is possible to use another composite absorbents (M') having a same construction of the above composite absorbents. The composite absorbents (M) is laid on the other composite absorbent (M') in such manner that the hot-melt adhesive layers contact to each other and being bonded together by an adhesive property thereof to form a composite structure (M/M').

Alternatively, an additional sheet material (N) may be interposed between said composite absorbents (M) and (M') and bonded thereto by an adhesive property of the hot-melt layers of the composite absorbents (M) and (M') to form a composite structure (M/N/M').

In another mode of the present invention, is provided a highly absorbent sheet in which solid SAP is generally distributed in layers almost all over one surface of a non-woven substrate with part of it in the voids of the non-woven fabric and another part of it exposed off the surface wherein the surface of said exposed solid SAP layer is covered by a dual fibrous network structure consisting of a first fibrous network of fine mesh comprising a hot-melt adhesive and a second fibrous network disposed on said first network and of coarser mesh compared with said first network comprising a hot-melt adhesive layer so that the highly absorbent sheet is much less apt to peel off than conventional products.

In the highly absorbent sheet thus covered by the dual fibrous network, the solid SAP needs not necessarily be bonded with each other by the fine cellulose fibers.

In the above-mentioned configuration, the first fibrous network is of fine mesh and the second fibrous network disposed on the first fibrous network is of coarse mesh, but the relation between the two may be reversed, that is to say, the first fibrous network may be of coarse mesh and the second fibrous network disposed on the first fibrous network may be of fine mesh.

Preferably, the fibers of a hot-melt layer of fine mesh are finer than those of a hot-melt layer of coarse mesh.

According to the present invention, there is provided a method for manufacturing a highly absorbent composite sheet by treating the surface of the highly absorbent composite sheet in which solid SAP is distributed in layers on one surface of a non-woven substrate comprising a combination of:

a first stage hot-melt processing step in which a hot-melt processing is conducted by means of a hot-melt feeding apparatus (A) which forms a first fibrous network of fine mesh consisting of hot-melt adhesive on the surface where said solid SAP is distributed; and a second stage hot-melt processing step in which a hot-melt processing is conducted by means of a hot-melt feeding apparatus (B) which forms a second fibrous network consisting of hot-melt adhesive of coarser mesh than said first fibrous network.

In a preferred aspect of the present invention said first stage hot-melt processing step is carried out with the hot-melt adhesive coated in an amount of 0.3 g/m² to 2 g/m² so that a first fibrous network of fine mesh is formed and said second stage hot-melt processing step is conducted with the hot-melt adhesive coated in an amount of 1 g/m² to 10 g/m² so that a second fibrous network is formed of coarser mesh than in the case of said first stage hot-melt processing step.

More preferably, said first stage hot-melt processing step is carried out with the hot-melt adhesive coated in an amount of 1 g/m² to 10 g/m² and said second stage hot-melt processing step is conducted with the hot-melt adhesive coated in an amount of 0.3 g/m² to 2 g/m² so that a second fibrous network is formed of finer mesh than in the case of said first stage hot-melt processing step.

A preferred form of said hot-melt feeding apparatus according to the present invention is two units of curtain spray type hot-melt feeding apparatus which is capable of forming a network of relatively fine mesh as combined in series with respect to the moving direction of said non-woven substrate.

By using a curtain spray type hot-melt feeding apparatus as said first stage hot-melt feeding apparatus a first fibrous network of fine mesh can be formed and by using a spiral coating type hot-melt feeding apparatus as said second stage hot-melt feeding apparatus a second fibrous network of coarser mesh than said first hot-melt layer can be formed.

Alternately, by using a spiral coating type hot-melt feeding apparatus as said first stage hot-melt feeding apparatus a first fibrous network of coarser mesh is formed and by using a curtain spray type hot-melt feeding apparatus as said second stage hot-melt feeding apparatus a second hot-melt layer of finer mesh than said first fibrous network is formed.

Furthermore, by using a curtain spray type hot-melt feeding apparatus as said first stage hot-melt feeding apparatus a first fibrous network of fine mesh can be formed and by using a line coating type hot-melt feeding apparatus as said second stage hot-melt feeding apparatus a second fibrous network of coarser mesh than said first fibrous network can be formed.

Alternately, it may sometimes be preferable that by using a line coating type hot-melt feeding apparatus as said first stage hot-melt feeding apparatus a first fibrous network of coarse mesh is formed and that by using a curtain spray type hot-melt feeding apparatus as said second stage hot-melt feeding apparatus a second fibrous network of finer mesh than said first fibrous network is formed.

A highly absorbent composite sheet according to the present invention is effectively used in absorbent products provided with a topsheet having liquid perviousness, an absorbent having liquid absorbency and liquid retention and a backsheet having liquid imperviousness as an absorbent having said liquid absorbency and liquid retention.

BRIEF DESCRIPTION OF THE DRAWINGS

FIG. 8A-1 is a photomicrograph showing the condition of a fibrous network formed on the surface of a film in case the coated amount of hot-melt adhesive is 1 g/m$^2$ (×30);

FIG. 8A-2 is a photomicrograph showing the condition of a fibrous network formed at the same conditions as in FIG. 8A-1 on the surface of a sample made by providing solid SAP layer on a non-woven substrate (×30);

FIG. 8B-1 is a photomicrograph showing the condition of a fibrous network formed on the surface of film in case the coated amount of hot-melt adhesive is 2 g/m$^2$ (×30);

FIG. 8B-2 is a photomicrograph showing the condition of a fibrous network formed at the same conditions as in FIG. 8B-1 on the surface of a sample made by providing solid SAP layer on a non-woven substrate (×30);

FIG. 8C-1 is a photomicrograph showing the condition of a fibrous network formed on the surface of film in case the coated amount of hot-melt adhesive is 5 g/m$^2$ (×30);

FIG. 8C-2 is a photomicrograph showing the condition of a fibrous network formed at the same conditions as in FIG. 8C-1 on the surface of a sample made by providing solid SAP layer on a non-woven substrate (×30);

FIG. 11 is a schematic plan showing several combinations of first stage and second stage hot-melt layers and the condition in which a highly absorbent sheet is covered by such combinations;

FIG. 12b is a side view showing the test machine shown in FIG. 12a;

FIG. 12c is a plan showing samples as tested by the test machine shown in FIG. 12a;

FIG. 14b is a sectional view of the unit for evaluation of an absorbent as shown in FIG. 1a;

DETAILED DESCRIPTION OF THE INVENTION

A highly absorbent composite sheet according to the present invention is described with reference to the accompanying drawings.

Figure 1:
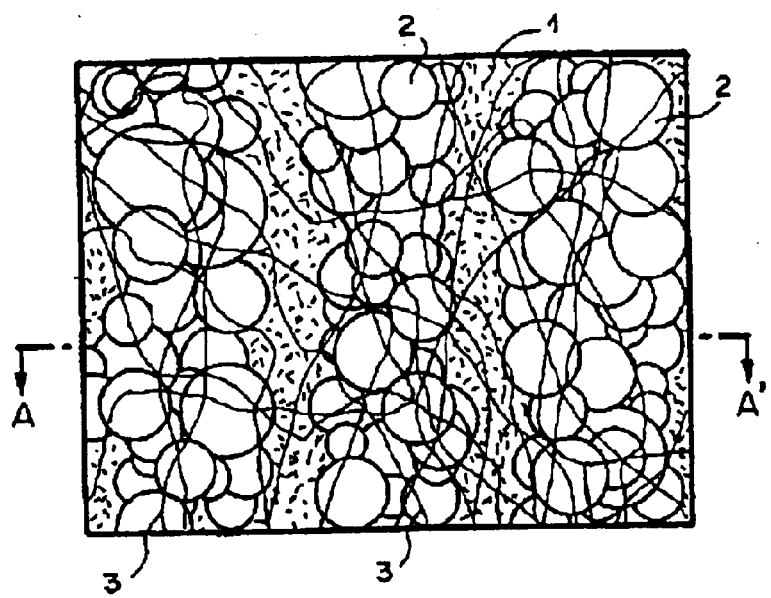
FIG. 1 is a plan schematically showing a highly absorbent composite sheet embodying the present invention.
Figure 2:
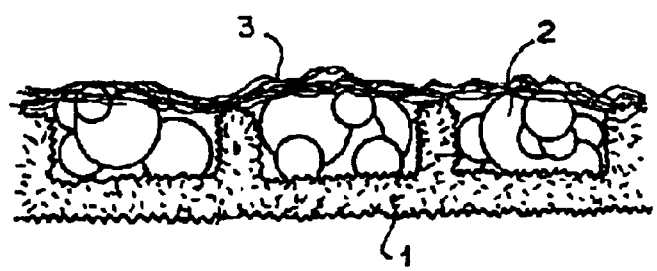
FIG. 2 is a sectional view taken along the line A–A' of FIG. 1.

FIG. 1 is a plan view showing a highly absorbent composite sheet embodying the present invention, and FIG. 2 gives a section taken along the line A–A' of FIG. 1. In each of the Figures, reference numeral 1 indicates non-woven substrate, 2 indicates solid SAP and 3 indicates a fibrous network constituted by thermally fusible component (hot-melt adhesive).

As clearly seen from FIG. 2, in the illustrated highly absorbent composite sheet, the surface of the non-woven substrate 1 is covered with the layer of solid SAP at major parts, but the remaining parts of the surface are contacted to the fibrous network 3 and bonded thereto. In other words, the highly absorbent composite sheet comprises first zones where the solid SAP 2 particles contact to the fibrous network 3, and second zones where the non-woven substrate 1 contact to the fibrous network 3 directly. The first zones constitute a distribution area and the second zones an acquisition area.

Non-woven substrate 1 as used in a highly absorbent composite sheet according to the present invention is preferably non-woven fabric comprising natural fiber, chemical or synthetic fiber, wood pulp, foamed material or the like and bulky and high in terms of voids so that it is outstanding in fluid dispersion. As such non-woven fabric a web made bulky by means of a publicly known method such as carded web, needle punching, spunlace and web folding can be applied. Among such webs, most preferable is non-woven fabric as obtained by raising fiber web and such web has a raised bulky structure. Specifically, such non-woven fabric as is relatively light and in addition bulky (for example, the weight is 10 g/m$^2$ to 100 g/m$^2$ and the apparent specific gravity is less than 0.2 g/m$^2$) is preferred.

Figure 3:
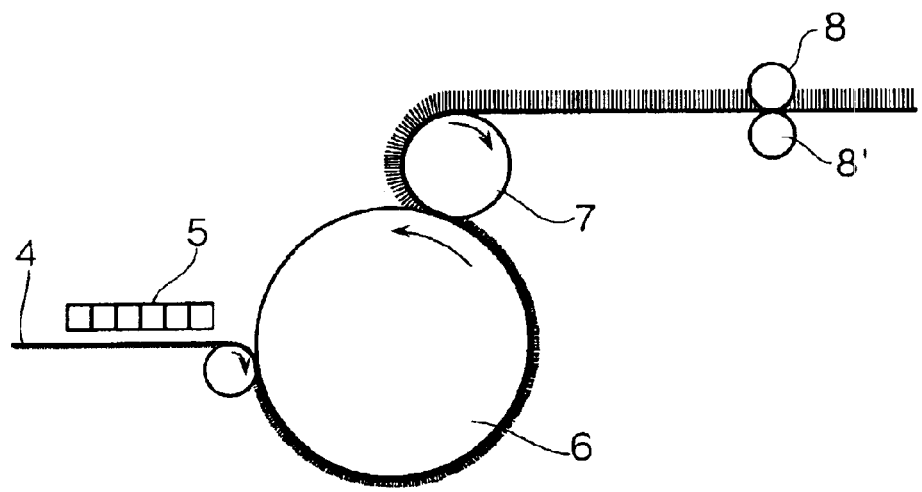
FIG. 3 is a schematic side view of an apparatus which can be used for raising a fiber web according to the present invention.

FIG. 3 shows an example of an apparatus for manufacturing a non-woven fabric having a bulky structure as uniformly raised by the raising treatment of a fiber web.

In FIG. 3 a fiber web 4 to be used as a starting material is preheated in a preheater 5 as needed (preheating zone). Then, the fiber web 4 is heated up to a temperature at which its constituting fibers are caused to soften, pressurized onto the surface of a heating roll 6 while rotated as driven in a direction shown by the arrow in FIG. 3, and, while moving, as it is, together with the surface, heated (heating and pressurizing zone). The fiber web 4 heated and pressurized is made to come into contact with the surface of a quenching roll 7 rotating in the reverse direction to the direction of the heating roll 6 so that the web 4 is peeled off the heating surface of the heating roll 6 (peeling zone). The fiber web 4 is then quenched as moving together with the surface of the quenching roll 7. The fiber web 4 while being pressurized in a half fused condition on the heating surface of the heating roll 6 is quenched and peeled off as being brought into contact with the roll 7 whereby the surface of the fiber web 4 adjacent to the surface of the quenching roll 7 is raised. The fiber web 4 which has passed over the quenching roll 7 is guided out to the outside of the system via grid rolls 8,8'.

Next, solid SAP is described below. As SAP, carboxymethyl cellulose, polyacrylic acid and its salts, crosslinked acrylate polymers, starch-acrylic acid graft copolymers, hydrolytes of starch-acrylonitiile graft copolymers, crosslinked polyoxyethylene, crosslinked carboxymethyl cellulose, polysulfonic acid type compounds, polyethylene oxide, polymers made by partly crosslinking water swelling polymers such as polyacrylic amide and polymeric resins having a capacity of forming hydrated gel such as copolymers of isobutylene and maleic acid are available. By drying any of these resins a polymeric resin as a base material can be obtained. Then, an after-treatment is applied in order to increase the crosslinked density of the surface of one of these particulate resins, and at the same time an antiblocking agent is added in order to inhibit the blocking propensity of powder due to its absorbing moisture.

In addition, a highly absorbent polymeric resin derived from microorganism of an incubation product coming from *Alcaligenes Latus*, or crosslinked amino acid, crosslinked amino acid polymer of biodegradable asparaginic acid is available as SAP for the present invention.

Examples of preferred forms of SAP are particles, granules, film, fibers, or non-woven fabric. In particular, particles, granules, flake, pellets, fibers (whose length is 10 mm or shorter) and short needles are more preferable, which can be dispersed uniformly in a dispersion medium. In this specification the term "SAP particles' is used for the sake of convenience to mean and include SAP in a variety of forms. Furthermore, the size of SAP particles is indicated by the diameter in the case of a sphere and by the length of the longest portion in case of any other form. In the present invention the preferred range of the size of SAP is 100 to 1000 $\mu$m.

Preferably, SAP particles are in all cases contained in the bulky structure of said non-woven substrate, i.e. in the voids formed between the constituting fibers. Depending on the amount of added resin and the bulkiness of a fiber web, however, part of the SAP may be exposed with no problem out of the surface of the non-woven substrate. That is because any such exposed resin remains bonded through hydrogen bonds of the fine cellulose fibers when it is in dry state. Such exposed resin, however, may turn into dust or powder when the non-woven substrate is abraded or bent as processed and, when it is wet, part of the resin might come out of the substrate. The amount of resin as contained in the non-woven substrate needs to be kept 50% by weight or more and preferably 70% by weight or more. From this point of view, it can be said that if higher concentration of resin as contained in the substrate is desired, bulkier non-woven substrate should be used accordingly.

In addition, of recent years, importance has been placed on such polymeric resins as are high in terms of gel stability, i.e. so-called dry polymeric resins are preferred. Thus, the evaluation of SAP has been discussed very much in terms of such measurements as absorption under load (AUL), performance under load (PUL) and liquid permeability of swollen gel (SFC). (U.S. Pat. No. 5,599,335 to Goldman et al.). As SAP as applied in the present invention, however, usually available polymeric resins of relatively low in the degree of cross-linking are used with no problem if they are stable to human and animal exudates and blood. Accordingly such resins as have 15 g/g or more in terms of AUL can be used with no problem.

Next, fine cellulose fibers are described below. As the fine cellulose fibers, finely ground pulp first of all and cellulose fibers of various sizes can be used, but preferably microfibrillated cellulose (hereinafter called "MFWC") having a water retention rate of at least 250% by weight is particularly good.

The fine cellulose fibers play the functions of a dispersion stabilizer for preventing the settling down of SAP particles and the coagulation with each other of SAP particles during the manufacture of a highly absorbent composite sheet according to the present invention and at the same time after the highly absorbent composite sheet has bee manufactured of a binder for binding SAP particles with each other and SAP particles with a non-woven substrate.

The fine cellulose fibers preferable for the present invention have an average fiber length of 0.01 to 0.1 mm and an average fiber diameter of 0.1 $\mu$m. MFC of microfine fibers having an apparent denier of 0.01 d or less obtained by opening wood pulp by means of high shearing force, an advanced version of such MFC, i.e. super microfibrillated cellulose ("S-MFC"), obtained by further opening such MFC, bacterial cellulose obtained as microorganism as raw material ("BC") and such fine cellulose fibers as are obtained by segregating open any of these fibers as they are diluted. Any of these fine fibers is of very small fiber size and possesses an advantage of retaining water at a high level as it contains water. A preferred example of such fine fiber type for the present invention has a water retention rate of at least 250% by weight as measured by Tappi test method. Such fiber type is described in detail in Japanese Patent Applications Laid Open Hei 08-284090 and Hei 11-170414.

Next, an example of bonding MFC to SAP particles in the present invention is described below:

Water and ethanol were added to 2.15% by weight water dispersion of S-MFC (manufactured by Tokushu Paper Mfg. Co., Ltd. under the trademark "Super Microfibrill Cellulose") so that water/ethanol dispersion (water/ethanol= 60 parts/40 parts) with the concentration of MFC of 0.8% by weight was prepared. Note that the water retention rate of MFC used was 320% by weight.

To this dispersion SAP (manufactured by Mitsubishi Chemical Co., Ltd. under the trademark of Aqua Pearl US-40) was added to prepare a two component slurry of 30% by weight SAP and 0.6% by weight MFC.

Then, said slurry was applied onto the surface of a non-woven substrate which has a relatively bulky structure by means of a coater in a way that the amount of said slurry coated was 150 g/m$^2$, and then immediately after suction and removal of remaining liquid were done, the substrate with the slurry applied on was heat pressed for several minutes by means of a heating roll heated at 180° C. and, further, dried in hot air so that a composite in which SAP particles were contained inside the bulky structure of the non-woven substrate was obtained.

Figure 4:
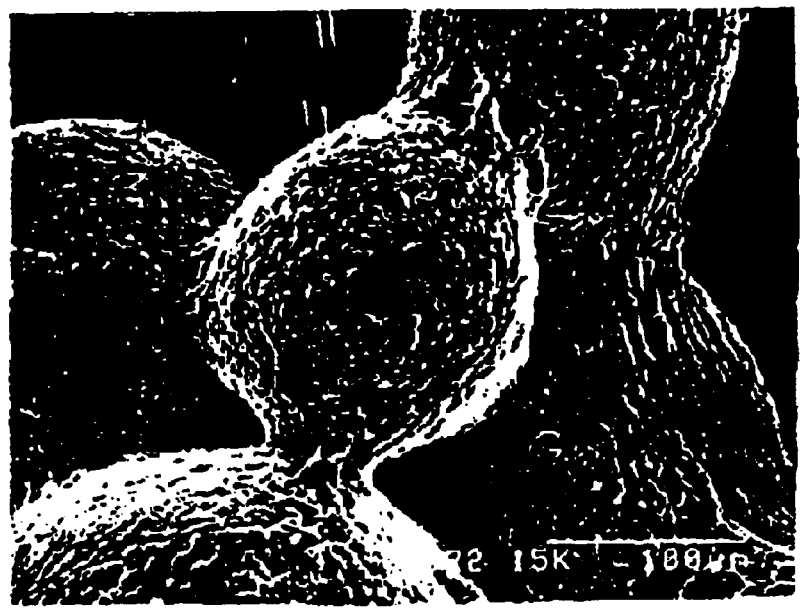
FIG. 4 is a photomicrograph of SAP particles and part of an MFC coating film in contact with the SAP particles (×240)

FIG. 4 is a photomicrograph of a typical example evidently showing the condition of MFC being in contact with the surface of such particles well covering the particles. As shown in FIG. 4, in the composite as obtained in the manner as described above, MFC is made covering in contact with the surface of SAP particles as it is in the shape of partly down-like film.

Next, a thermally fusible component used for the present invention is described below:

In the present invention, a fibrous network is formed of a thermally fusible component.

The covering effect of the fibrous network is shown below:

First of all, by covering SAP particles with the fibrous network, the SAP particles are further stably held on the non-woven substrate of the composite and thus are prevented from peeling and coming off the composite. For example, SAP particles are prevented from peeling and coming off the composite when the particles are dry during the steps of manufacturing the composite, slitting, taking up or assembling into an absorbent product. In addition, when SAP particles are wet and swollen, fibrous network serves to maintain the holding capacity of the non-woven substrate even if the SAP particles swell and the non-woven substrate swells, and as a result, the SAP particles are prevented from peeling and coming off the composite. Furthermore, when the composite is wound onto a roll or stored as it is on the roll, the fibrous network serves to prevent any blocking from taking place on the surface of the absorbent layer (SAP layer) of the composite and the backside of the non-woven substrate which is adjacent to the absorbent layer in contact with each other.

A thermally fusible component according to the present invention is a hot-melt adhesive. As described in the above, the thermally fusible component is in thin and fine film, fiber and preferably finely fibrillated form and covers the surface of SAP particles. These preferred forms of the thermally fusible component are called "fibrous".

In the present invention, in order to improve the property of forming sticky threads (hereinafter referred to as "thread forming property") and extensity of the hot-melt adhesive, an elastomeric component such as ethylene—vinyl acetate copolymer (EVA), styrene-isobutylene-styrene copolymer (SIS), and styrene-ethylene-butadiene-styrene copolymer (SEBS) can be added. As a result of the addition, the effect of covering the SAP particles is further improved. That is to say, the fibrous hot-melt adhesive is extended as it is threaded as the SAP is swollen. As a result, the SAP particles are not prevented from swelling and such swollen SAP particles are prevented from peeling and coming off the composite.

In this case as a hot-melt adhesive such adhesive as is non-tucking and easy to turn into fibers and in addition to fibrillate is used. Particularly preferable is a hot-melt adhesive with ethylene-vinyl acetate copolymer as the main component. The content of vinyl acetate in an ethylene-vinyl acetate copolymer is very important for the formation of its thread forming property and making into fibers, and the molecular weight of vinyl acetate affects its dischargeability and making into fibers to a great extent. The higher the content of vinyl acetate in an ethylene-vinyl acetate copolymer, the better the result in such terms. For example, the content of vinyl acetate should be 15% by weight or more, and preferably 20 to 40% by weight. The molecular weight which is an indicator of dischargeability of a liquid if expressed in terms of thermal fluidity rate in MFR (g/10 min) 200 to 400 g/10 min for a conventional ethylene-vinyl acetate copolymer type hot-melt adhesive and in the present invention the MFR is 200 g/10 min or smaller and preferably 50 to 150 g/10 min.

Figure 5:
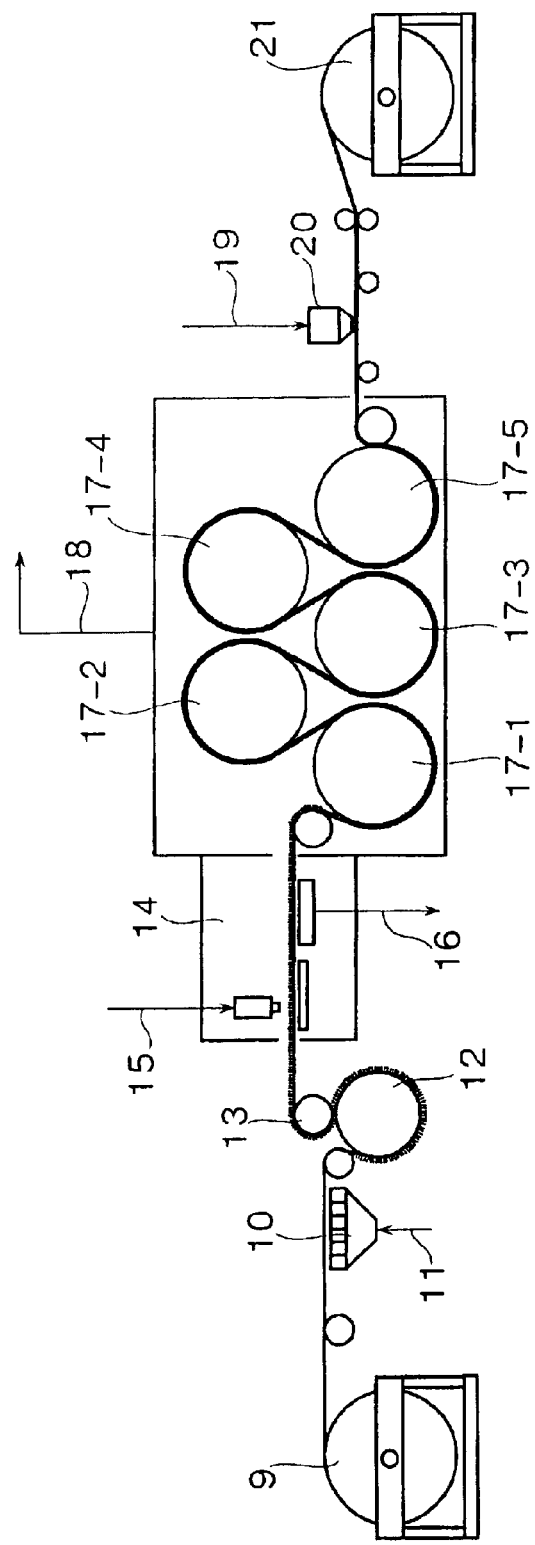
FIG. 5 is a flow sheet showing an example of an apparatus for manufacturing a highly absorbent composite sheet according to a method of the present invention.

Next, a specific example of a method for making a highly absorbent composite sheet according to the present invention is described with reference to FIG. 5.

Non-woven substrate, i.e. fiber web, is taken out of an unwinder 9. As necessary hot air fed via a hot air line 11 by means of a preheater 10 is blown to the fiber web as taken out of the unwinder 9 to preheat the fiber web. The fiber web which was compressed is now made swollen and bulky by this preheating (preheating zone).

The thus preheated fiber web is heated as being in contact with a heating roll 12 and then cooled as being in contact with a cooling roll 13. As in the case of FIG. 3 described in the above, the surface of the fiber web which is made in contact with the heating roll 12 is raised (heating and cooling zone).

The fiber web as raised is sent to a coater 14 where SAP slurry fed via a SAP slurry line 15 is applied onto the raised surface of the fiber web. In succession, liquid in the web is suctioned together with atmosphere gas via a suction line 16 and a highly absorbent composite sheet which is not yet dried is formed (coating zone). Note that the SAP slurry is prepared in the manner described in the above.

Undried highly absorbent composite sheet is then heated as passing through a series of drying rolls 17-1 to 17-5 in succession and vapors of water and solvent as evaporating from the sheet are discharged out of the system via a discharge line 18 (hot air drying zone).

Hot-melt adhesive as fed from a hot-melt line 19 is applied as blown onto the surface of the highly absorbent composite sheet thus dried by hot air which contains SAP particles by means of a curtain spray apparatus 20 whereby a fibrous network of hot-melt adhesive is formed. The highly absorbent composite sheet as covered is taken up on a winder 21.

Figure 6:
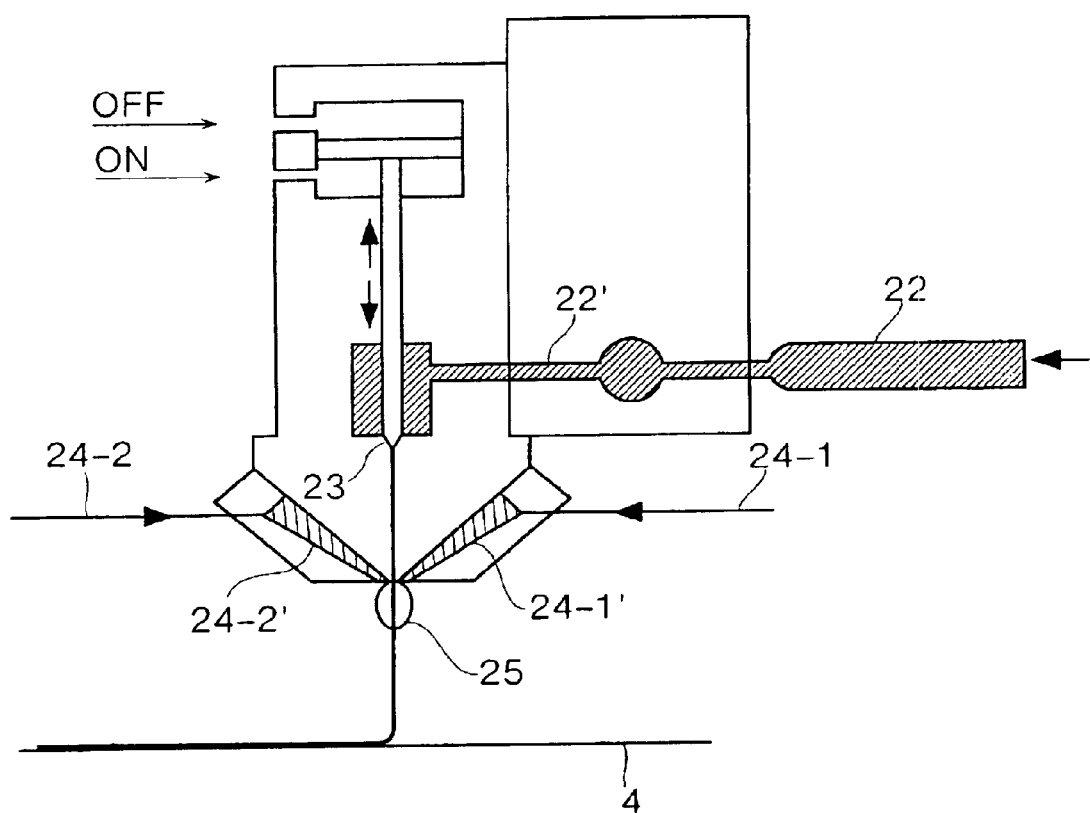
FIG. 6 is a sectional view schematically showing a curtain spray apparatus which can be applied to the apparatus of FIG. 5.

In the present invention as a coating apparatus for hot-melt adhesive such apparatus is preferable as is capable of forming fine fibers with a small amount of hot-melt adhesive, blowing these fibers onto the surface of the absorbent composite sheet which contains SAP particles so that the surface is well covered with the resultant fibrous network. More specifically, it is preferably a non-contact type apparatus, e.g. a spray type, a spiral spray type, and a melt blow type. More preferable apparatus is a melt blow type capable of extending hot-melt adhesive by means of hot air so that the hot-melt adhesive is made into fine streams and fibers by a nozzle. This melt blow type apparatus is also called a curtain spray type or a slot spray type. Hereunder, an example of a curtain spray type apparatus 20 for hot-melt adhesive is shown in FIG. 6.

An apparatus of this type is provided with a leading inlet 22 and a leading pipe 22' for hot-melt adhesive, a valve 23 for introducing hot-melt adhesive, hot-melt adhesive distributing nozzle (not shown), a plurality of air inlets 24-1, 24-2, leading pipes 24-1', 24-2' and a outlet 25 for a flow of fiber/air mixture.

The valve 23 for introducing hot-melt adhesive is disposed on the tip of the leading pipe 22' and controls the flow of hot-melt adhesive fed from the leading pipe 22'.

The hot-melt adhesive distributing nozzle is disposed adjacent to the valve 23 for introducing hot-melt adhesive and forms a film of the hot-melt adhesive by distributing and feeding the hot-melt adhesive in the direction of the width of the covering as fed from said valve 23 for introducing hot-melt adhesive.

The plurality of air inlets 24-1', 24-2' disposed having the hot-melt distributing nozzle in between function to blow hot air to the facing surfaces of the hot-melt adhesive film through the plurality of air inlets 24-1', 24-2' to make the film into mist-like form and fibers.

The hot-melt adhesive thus made into fibers is made into a curtain-like form and deposited on the fiber web 4.

Figure 7A:
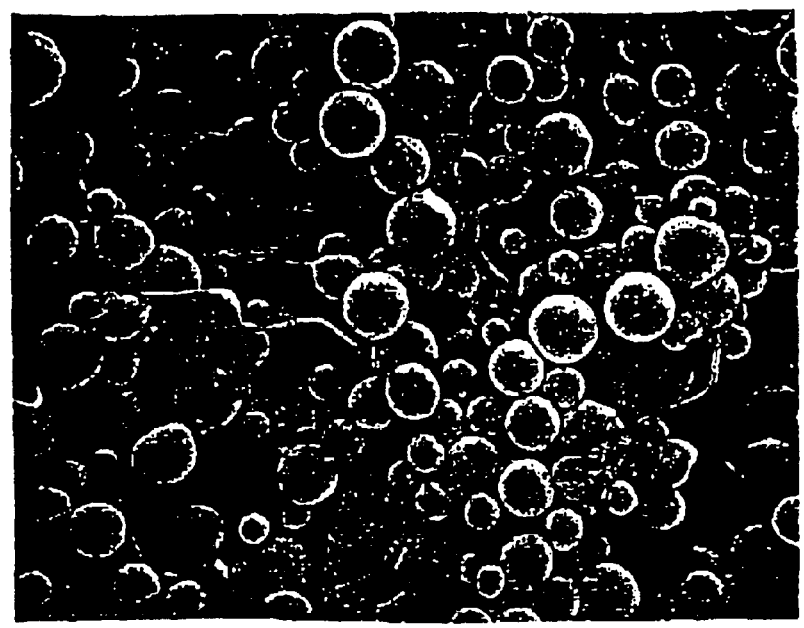
FIG. 7a is a photomicrograph of the surface of a sheet not treated by the surface treatment by means of hot-melt adhesive (×30)
Figure 7B:
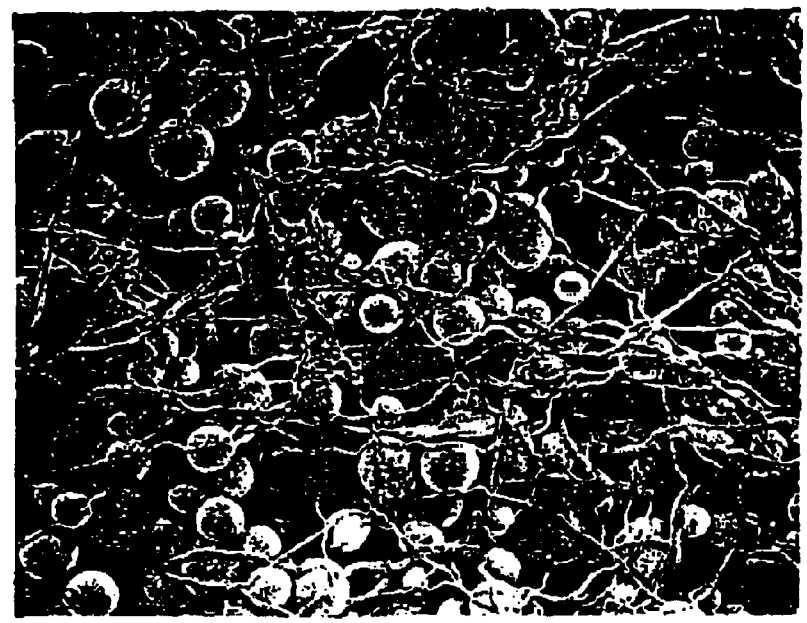
FIG. 7b is a photomicrograph of the surface of a sheet treated by the surface treatment by means of hot-melt adhesive (×30)

FIG. 7a is a photomicrograph showing the absorbent composite the surface of which is not treated with hot-melt adhesive and FIG. 7b is a photomicrograph showing the condition of hot-melt adhesive is deposited on the absorbent composite sheet the surface of which is treated with hot-melt adhesive.

Figures 1, 8A:
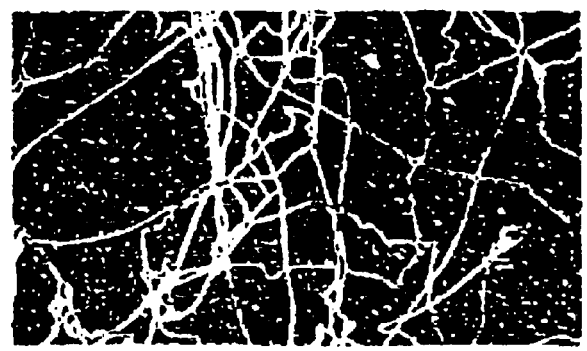
Figures 2, 8A:
Figures 1, 8B:
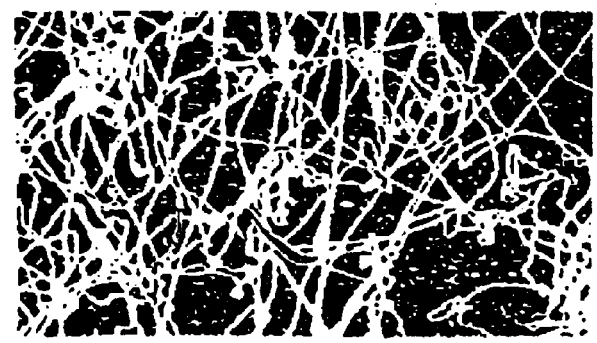
Figures 2, 8B:
Figures 1, 8C:
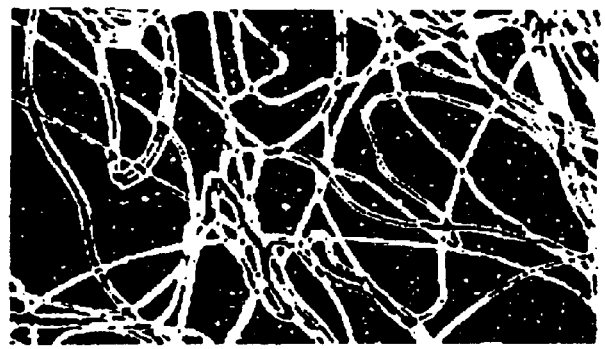
Figures 2, 8C:
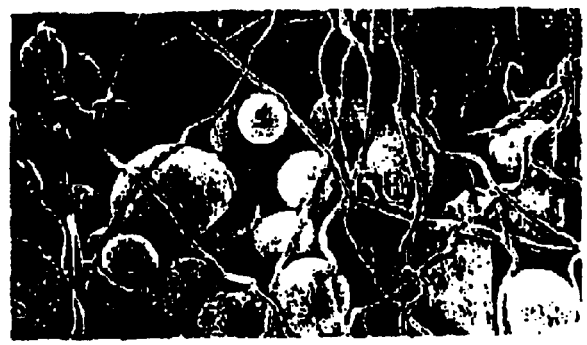

Several experiments were conducted to investigate the relation between the coated amount of hot-melt adhesive and the condition of the resultant fibrous network. The case that the coated amount is 1 g/m² is shown in FIG. 8A-1, the case of 2 g/m² is in FIG. 8B-1, the case of 5 g/m² is in FIG. 8C-1. In case the SAP coated surface of the fibrous network is coated, the condition shown in FIG. 8A-2 results in case 1 g/m² is coated, the condition shown in FIG. 8B-2 results in case 2 g/m² is coated, and the condition shown in FIG. 8C-2 results in case 5 g/m² is coated.

As the coated amount of hot-melt adhesive is increased, the density of the resultant fibrous network becomes higher and the diameter of the constituting fibers becomes coarser. A coated amount of hot-melt adhesive is normally 0.2 to 10 g/m², and preferably 0.2 to 5 g/m². In case the amount is less than 0.2 g/m², the constituting fibers existent in the network become sparse and conversely if the amount is more than 10 g/m², the fibers get filmy in parts.

Returning to FIG. 1, in a highly absorbent composite sheet according to the present invention, not only SAP particles cover the surface of a non-woven substrate very well, but also a plurality of covered portions and a plurality of uncovered portions exist as mixed. The fibrous network prepared with hot-melt adhesive made fibrous covers both exposed portions of the surface and portions forming a composite of SAP particles and a non-woven substrate.

In general, the bonding force of a substrate to hot-melt adhesive is higher than that of SAP particles to hot-melt adhesive. As a result, as SAP particles become swollen when wet, hot-melt fibers also are extended, but an anchoring portion formed by bonding of a substrate to hot-melt adhesive serves to hold SAP particles stably. That is to say, when SAP particles get swollen, hot-melt fibers hold SAP particles in a manner that SAP particles are allowed to move to some extent. In this case, however, the affinity of hot-melt adhesive to a non-woven substrate becomes an important element. That is to say, as the affinity of hot-melt adhesive to a non-woven substrate becomes higher, the retention of SAP particles varies. In the case that hot-melt adhesive is ethylene-vinyl acetate copolymer, preferable substrates are polyethylene terephthalate (PET), polyethylene (PE)/ polyethylene terephthalate (PET) and viscose rayon.

Next, another embodiment of the present invention is described below:

In this embodiment, a highly absorbent composite sheet according to the present invention is made composite by combining one surface of a non-woven substrate with a solid SAP layer as described above, and there are two models of such structure.

FIG. 9 show examples of such models of supporting SAP particles on a non-woven substrate as applied to the present invention.

Model No. 1

Figure 9A:
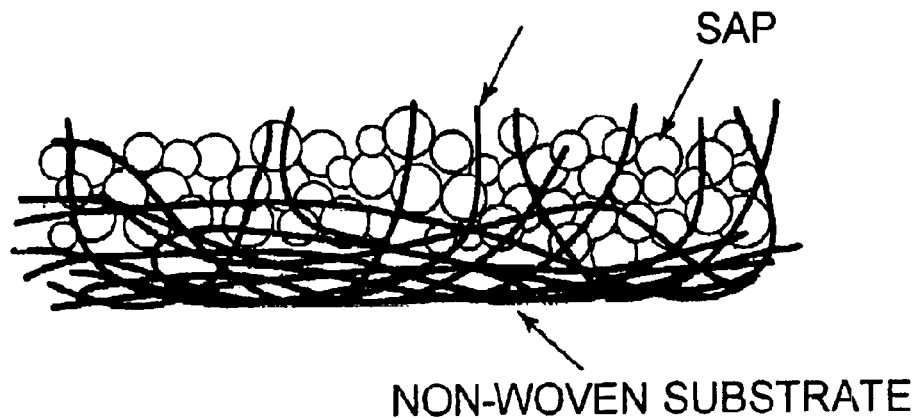
FIG. 9a is a sectional view showing a model of the manner in which SAP particles are supported on a non-woven substrate as applied in the present invention.

Model No. 1 shown in FIG. 9a is a condition where a majority of SAP particles exist as contained in the voids formed by the fibers of a non-woven fabric with a part of the fibers constituting the fiber layer of the non-woven fabric existent on the surface and a part of the SAP particles also exposed. In the case of such bulky non-woven substrate, 50% or more of the SAP particles is in general contained between and among the fibers. Model No. 2

Figure 9B:
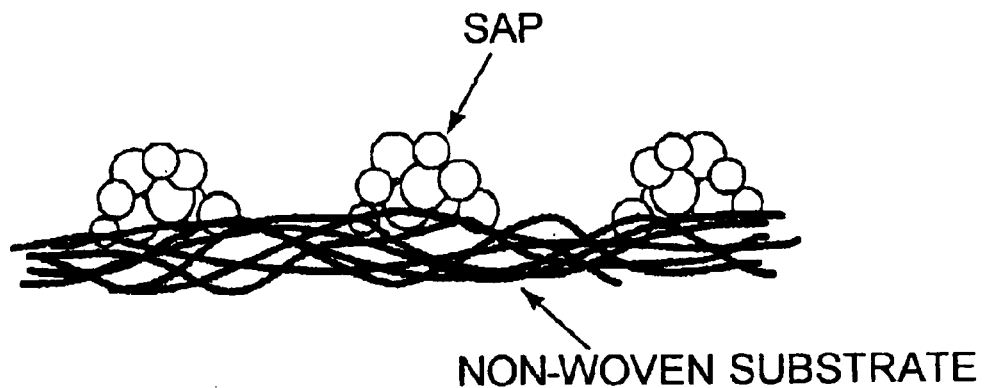
FIG. 9b is a sectional view showing another model of the manner in which SAP particles are supported on a non-woven substrate as applied in the present invention.

On the other hand, in Model No. 2 shown in FIG. 9b a majority of SAP particles is exposed on the surface of the non-woven fabric, and SAP particles layers and parts of non-woven fabric with no SAP particles contained co-exist. A non-woven substrate of this type is relatively flat, and the amount of SAP particles contained between and among the fibers of the non-woven fabric is in general less than 50% by weight.

Models Nos. 1 and 2 are different from each other in terms of the condition of hot-melt material as made into fibers existing. That is to say, in Model No. 1, hot-melt material made into fibers is bonded stably with those existent on the surface of the fibers constituting the fiber layer of the non-woven substrate as the hot-melt material covers SAP particles. On the other hand, in Model No. 2, hot-melt material made into fibers is covers exposed SAP particles and at the same time bonded stably with the portion of the non-woven substrate which has no SAP particles, and accordingly, the stability of the covering condition is affected by the bonding of the hot-melt layer and the non-woven substrate.

The present invention is applicable to the structures shown in both of the Models. In either structure, the surface of the non-woven substrate which contains SAP particles is covered by a dual fibrous network hot-melt layer consisting of a first hot-melt layer of a fine mesh fibrous network and a second hot-melt layer of coarser mesh fibrous network than the first hot-melt layer more effectively than in the case of a single hot-melt layer.

Next, various conditions of hot-melt layers as applied to the present invention are explained below:

① About the Fineness of Mesh Size of Fibrous Network Hot-melt Layer

In the present invention the term "fibrous network" is used to mean a network wherein hot-melt layers are constituted by many fibers as entangled with each other unlike a conventional hot-melt treatment wherein hot-melt layer works to cover in a film-like form. Such fibrous network means a uniform covering, not preventing the permeation of liquid and the swelling of SAP particles.

Preferred degree of fineness of fibrous network depends on the size of SAP particles used and the condition of such SAP particles in existence. That is to say, the preferred degree of fineness is determined by the types of SAP particles used and the condition of the SAP particles, i.e. whether they are dry or wet. The particle diameter of SAP particles when they are dry is small in case of spherical SAP particles as manufactured by reverse phase suspension polymerization and of particulate SAP as obtained by grinding gel and specifically approximately 50 μm to 300 μm in general. The particle diameter of SAP particles in flake or palletized form is 300 μm to 1000 μm. SAP particles in this range of diameter expand approximately three times in diameter if swollen absorbing urine. Accordingly, the diameter of spherical SAP particles is 150 μm to 1000 μm and that of flake-like or palletized SAP particles is 1000 μm to 3000 μm.

In order to achieve the surface stability of SAP particles, i.e. to prevent SAP particles of small diameter existent on the surface from peeling or coming off due to abrasion or bending of a highly absorbent composite sheet, it is more effective to have a structure of fine mesh fibrous network of fine fibers rather than to have a high strength of fibers of hot-melt layer. On the other hand, in order to prevent swollen SAP particles from peeling or coming off when wet, it is more important to have coarse fibers, i.e. a high strength of fibers even if the fibrous network is of coarse mesh.

It is not easy to achieve mutually contradicting requirements through one time hot-melt treatment. In the present invention by combining an apparatus for feeding hot-melt to make fine mesh of fine fibers (A) and an apparatus for feeding hot-melt to make coarse mesh of coarse fibers (B), the above-mentioned contradicting requirements is satisfied whereby the surface can be treated with SAP particles much less peeling or coming off whether they are dry or wet. Whether fibers constituting a hot-melt fibrous network are coarse or not and whether the mesh structure of the hot-melt fibrous network is coarse or not are determined by the diameter of a nozzle for feeding hot-melt material, the frequency of feeding, and the amount of the material fed. If the diameter of the nozzle and the interval of feeding are the same, they are determined by the amount of the material fed and the amount of air charged.

In an apparatus (hereinafter called "A") for forming a fibrous network of fine mesh and fine fibers, the coated amount is $0.3/m^2$ to $2$ $g/m^2$, and preferably approximately $0.5$ $g/m^2$ to $1$ $g/m^2$. If the amount is less than $0.3$ $g/m^2$, the coating cannot be uniform and if it exceeds $2$ $g/m^2$, a coarse network is likely to result.

On the other hand, in an apparatus (hereinafter called "B") for forming a fibrous network of coarse mesh and coarse fibers, the coated amount is $1/m^2$ to $10$ $g/m^2$, and preferably $1$ $g/m^2$ to $5$ $g/m^2$. If the amount exceeds $10$ $g/m^2$, the hot-melt material gets too much so that the swelling of SAP particles may be impeded.

Figure 10:
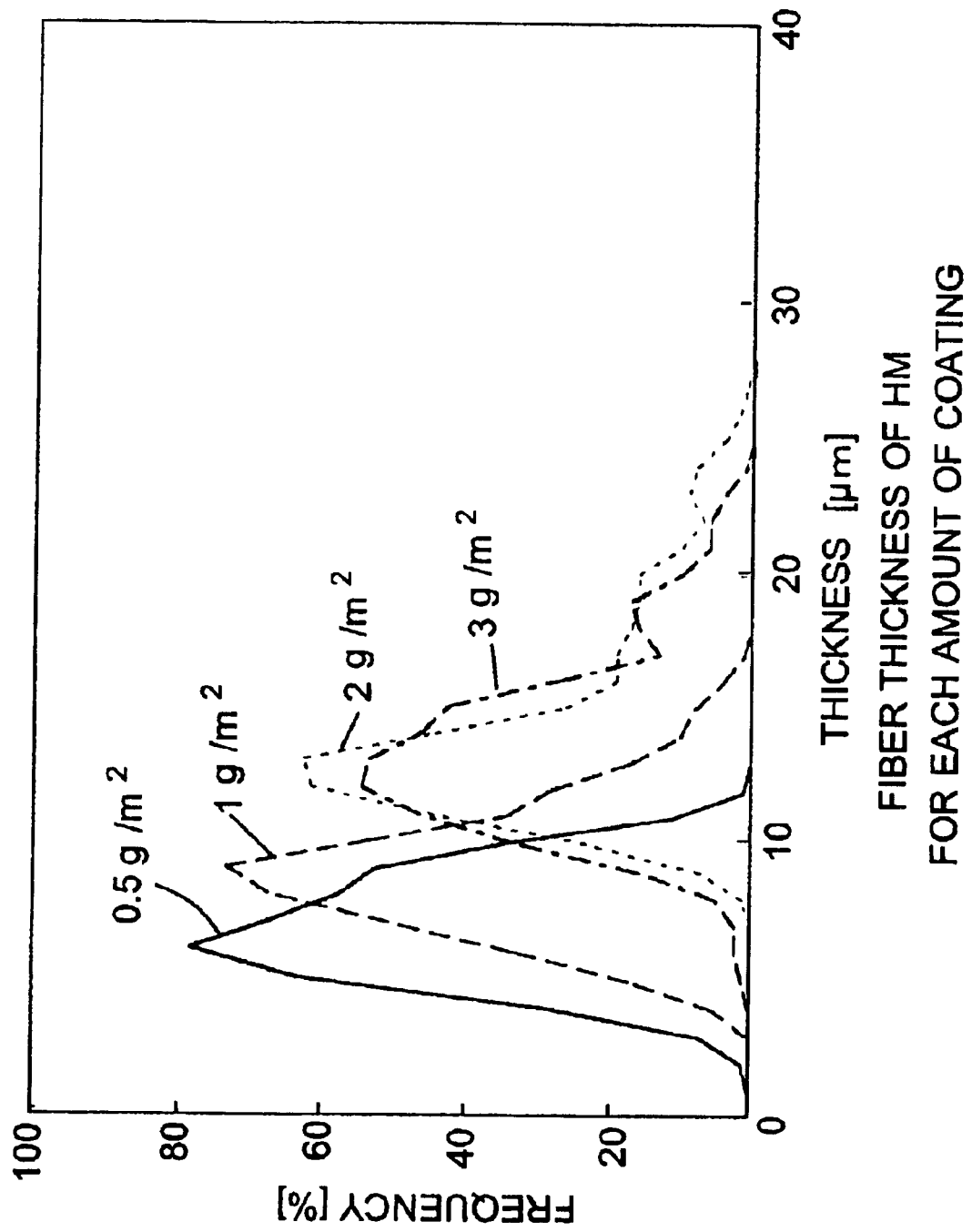
FIG. 10 is a graph obtained by plotting the measurements of the relation between the frequency (%) and the thickness ($\mu$m) of hot-melt fibers.

FIG. 10 is a graph obtained by plotting the measurements of the relation between the coated amount of hot-melt material and the average denier of resultant hot-melt fibers when the same hot-melt material is added at the same conditions. In FIG. 10, the frequency in % on the abscissa means the frequency of fibers existing in a unit length which is approximately proportional to the coated amount of hot-melt material. On the ordinate, the average diameter of hot-melt fibers for each coated amount is shown in $\mu m$.

From the measurements it is known that as the coated amount of hot-melt material gets more, the coarseness of the resultant hot-melt fibers becomes higher.

The term "fine fibrous network" used in the present invention means a fibrous network consisting of the fibers whose diameter is approximately $3$ $\mu m$ to $10$ $\mu m$ as amplified by a microscope and measured, and the term "coarse fibrous network" used in the present invention means a fibrous network consisting of the fibers whose diameter is approximately $10$ $\mu m$ to $50$ $\mu m$. However, the fibers in a fibrous network are not like synthetic fibers spun, and as such have no uniform diameter and a wide diameter distribution. Therefore, the above-mentioned values are just average.

② Roles of First Stage and Second Stage Hot-melt Surface Treatments

The effects have so far been described of the hot-melt surface treatment combining hot-melt feeding apparatuses (A) and (B). Hot-melt surface treatment of this type can be made in three or more multi stage so that even better result may be achieved. From the viewpoint of economical efficiency, however, the two-stage treatment is sufficient in many cases.

In the combination of hot-melt feeding apparatuses (A) and (B), whether in the first stage treatment a fibrous network of fine mesh is intended to be made or a fibrous network of coarse mesh is intended to be made, i.e. order of combined fineness and coarseness, is dependent on the conditions of a non-woven substrate and aspects of hot-melt. The order of making fine and coarse fibers in a fibrous network should be appropriately selected by taking various conditions into consideration.

③ Hot-melt Materials Used

Requirements of a hot-melt material used are first of all that the material can be made into fibrous network as easily as possible, secondly that it is free from tucking problem, and thirdly that the material can be bonded with a non-woven substrate and its constituting components as easily as possible.

Since the ease of making into a fibrous network is dependent on such factors as the degree of polymerization and the melt index of a polymer used, the selection of appropriate polymers is very important. The tacking problem is a problem inherent in a treatment of this type, and if there is a tacking problem involved, when a plurality of highly absorbent composite sheets are folded, such sheets as are adjacent to each other are bonded on the backside of the constituting non-woven substrate, i.e. so-called blocking phenomenon takes place. Preferably, therefore, hot-melt materials of less tacking property are selected. In the combination of the first and second stage treatments, a hot-melt material for the second stage treatment is desired to be of less tacking property, but a hot-melt material for the first stage treatment can be less strict in terms of tacking property because the surface of the material is covered by the first stage hot-melt layer.

Representative hot-melt materials of less tacking problems are of E.V.A. type, i.e. ethylene-vinyl acetate copolymers. The content of vinyl acetate is very important in terms of thread forming property and making into fibers. In addition, the molecular weight of vinyl acetate affects the amount of discharging and the making into fibers to a great extent. The more is the amount of vinyl acetate in an ethylene-vinyl acetate copolymer, the better is the resultant performance. For example, the amount of vinyl acetate is 15% by weight and preferably 20% to 40% by weight. The molecular weight as expressed in terms of thermal fluidity coefficient (MFR in g/10 min) to indicate the dischargeability of liquid is 200 to 400 g/10 min in a hot-melt material of conventional ethylene-vinyl acetate copolymer. In the present invention the molecular weight is 200 g/10 min or less and preferably 50 to 150 g/10 min.

To such hot-melt materials as are acceptable even if they have a tacking tendency, such olefins as amorphous polyethylene and polypropylene and rubber components such as S.E.B.S. (styrene, ethylene, butadiene-styrene block copolymer), S.I.S. (styrene, isobutylene, styrene block copolymer) can be added.

④ Affinity of Non-woven Substrate to Hot-melt Layer

In the present invention the objects of treating the surface of a highly absorbent composite sheet or a non-woven substrate with dual hot-melt layer are first to cover uniformly the surface of a highly absorbent composite sheet with a fibrous hot-melt layer and secondly to bond well the coated hot-melt layer to the surface of the non-woven substrate or to the fibers constituting the non-woven fabric.

In order to achieve the first object, as mentioned in the above, a dual network structure consisting of fine mesh and coarse mesh is formed. To achieve the second object, it is important to realize a good affinity of the hot-melt layer to the non-woven substrate or to the fibers constituting the substrate. To obtain a ideal bonding, it is better to have identical components of a hot-melt material and a non-woven substrate. For example, hot-melt material of polypropylene type is used on a polypropylene non-woven substrate with good results.

However, since it is generally the case that the component of a hot-melt material is different from the fiber component, it is desirable to select a compatible combination. For example, if a hot-melt material of E.V.A type is used, polyester fiber and nylon filament can be well bonded. If such hot-melt material is used for bonding polypropylene fiber, a relatively strong bonding can be attained. But in bonding polyethylene and cellulose fibers, the result tends to be rather weak unless sufficiently compressed. In such case it is desirous to take a step for stabilizing the bonding by mixing polyester fiber to polyethylene or cellulose fiber.

Next, examples of patterns of combining hot-melt layers are described below:

Several cases of combining first and second stage hot-melt layers and the resultant condition of covering are shown as examples 1, 2 and 3, respectively, in FIG. 11.

Case 1 is an example wherein a curtain spray is applied for the first and the second stage and in the first stage fine hot-melt fibers are densely combined and in the second stage coarse hot-melt fibers are loosely combined for the surface treatment.

Case 2 is an example wherein fine and dense curtain spray in the first stage is combined with coarse and loose spiral coat in the second stage.

Case 3 is an example wherein in the first stage a reinforcing line is formed of hot-melt fibers by a line coating and in the second stage fine and dense curtain spray is combined.

In order to ascertain objectively the degree of SAP particles being stably held without peeling and coming off under various conditions in a highly absorbent composite sheet whose surface has been treated according to the present invention, the present inventors have prepared a stability tester as shown in FIGS. 12a to 12d. Using the tester, the stability of SAP particles as contained in a non-woven substrate was measured. In the examples to be described later in this specification the values indicated as "Stability of SAP" are those measured by the tester.

Figure 12A:
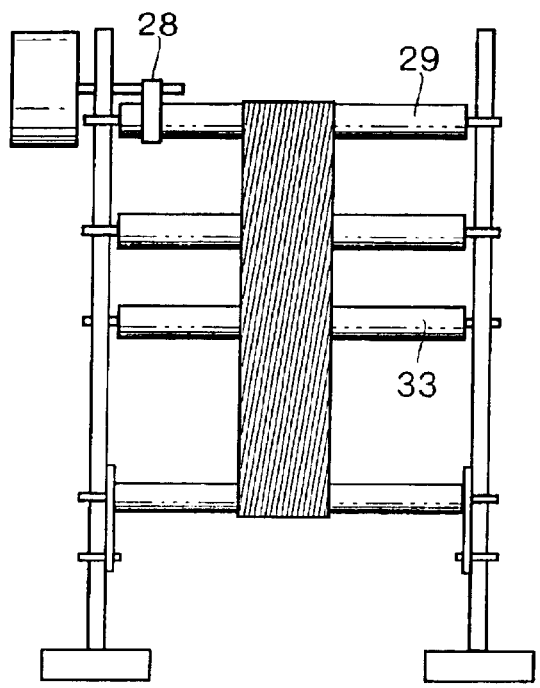
FIG. 12a is an elevation view showing a test machine for evaluating the stability of SAP particles.
Figure 12B:
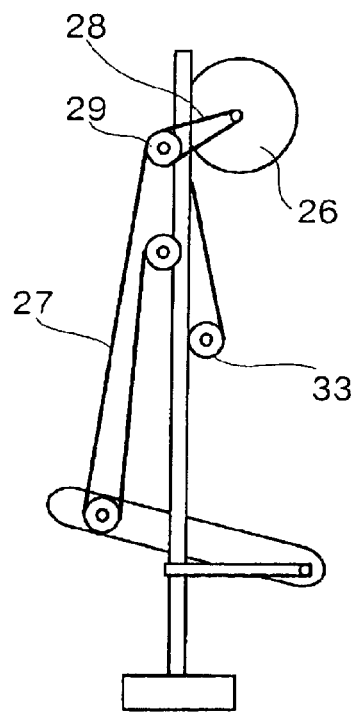
Figure 12C:
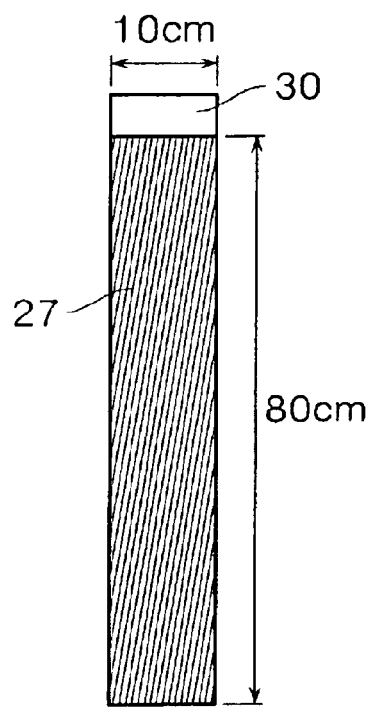

In FIGS. 12a to 12c, reference number 26 is a motor, 27 is a sample of a highly absorbent composite sheet to be evaluated, 28 is a driven roller, 30 is a tape, 31 is the surface of the sample which has been coated, 32 is its backside, 33 is a tension roller.

Figure 16:
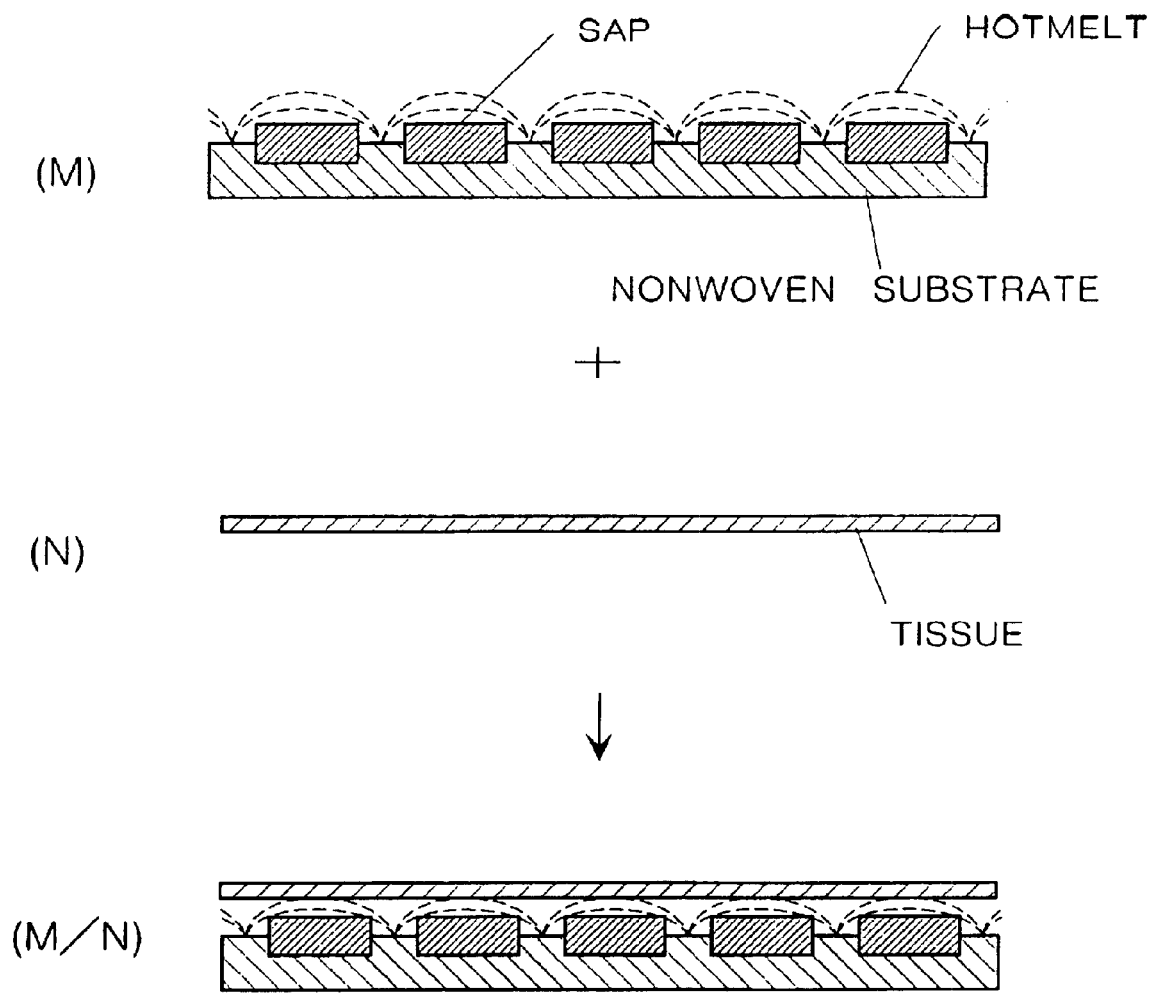
FIG. 16 shows the steps of manufacturing a modification of the highly absorbent composite sheet embodying the present invention.

So far SAP, nonwoven fabric and the hot-melt surface treatment of composite absorbent have been described. Applying of a hot-melt adhesive used for treating the surface of the composite absorbent to bonding integrally with still other material is also an important embodiment of the present invention. A first modification of the embodiment can be utilized as a bonding means in the step of converting a composite absorbent according to the present invention into an absorbent product for integrally bonding, on the surface where SAP exists, other material such as tissue, diffusion sheet, acquisition layer, topsheet or backsheet. In such case any of abovementioned material is placed as folded on the surface where SAP exists which has been treated with non-tuck hot-melt, heated and compressed so that the integral bonding is achieved. Such integral bonding is sometimes achieved at the time when the hot-melt surface treatment is performed in the step of manufacturing a composite absorbent according to the present invention in which case the hot-melt used therefore needs not be of non-tuck type but can be of rubber type having room temperature stickiness. FIG. 16 is prepared for illustrating this first modification by integrally bonding for example tissue (N) to a composite absorbent (M) so that the hot-melt existent on the surface of (M) is utilized, a structure of (M/N) can be obtained.

Figure 17:
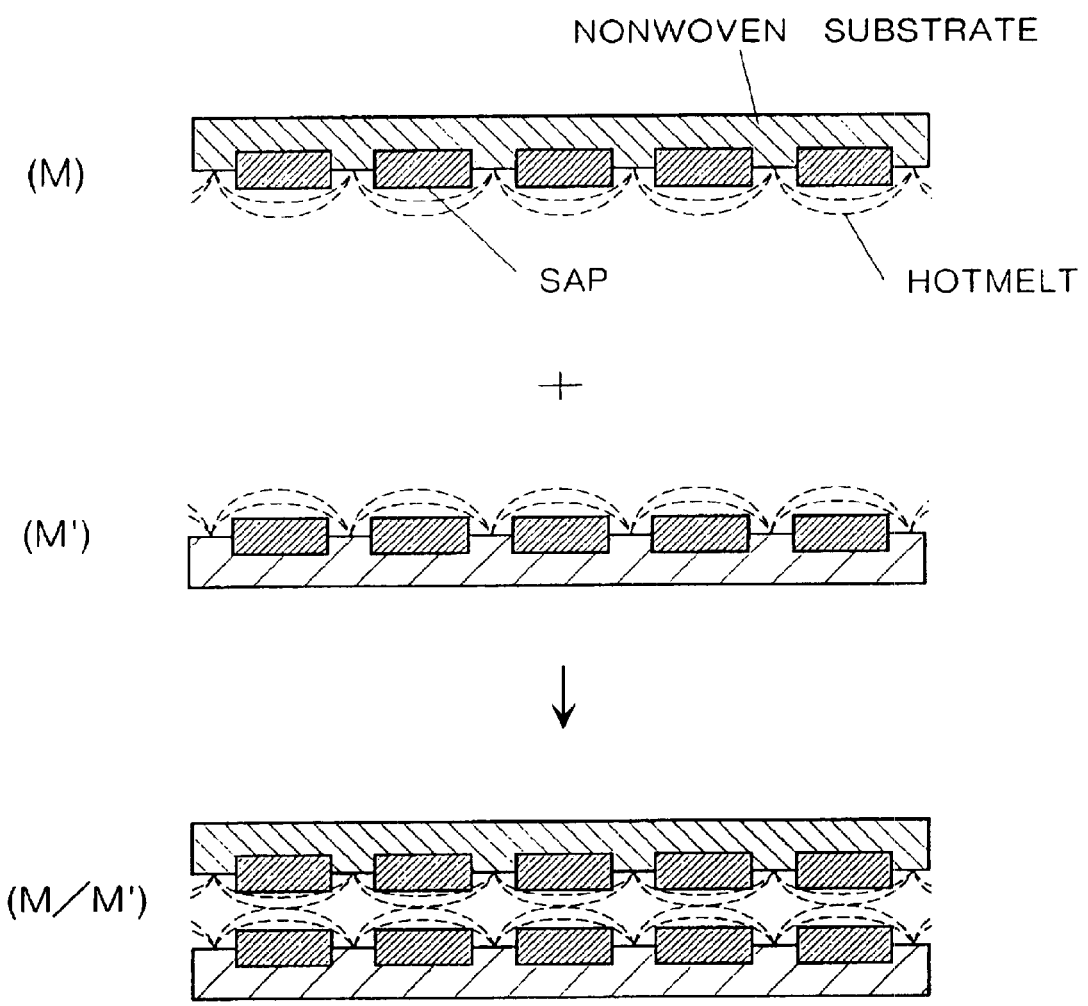
FIG. 17 shows the steps of manufacturing a further modification of the highly absorbent composite sheet embodying the present invention.
Figure 18:
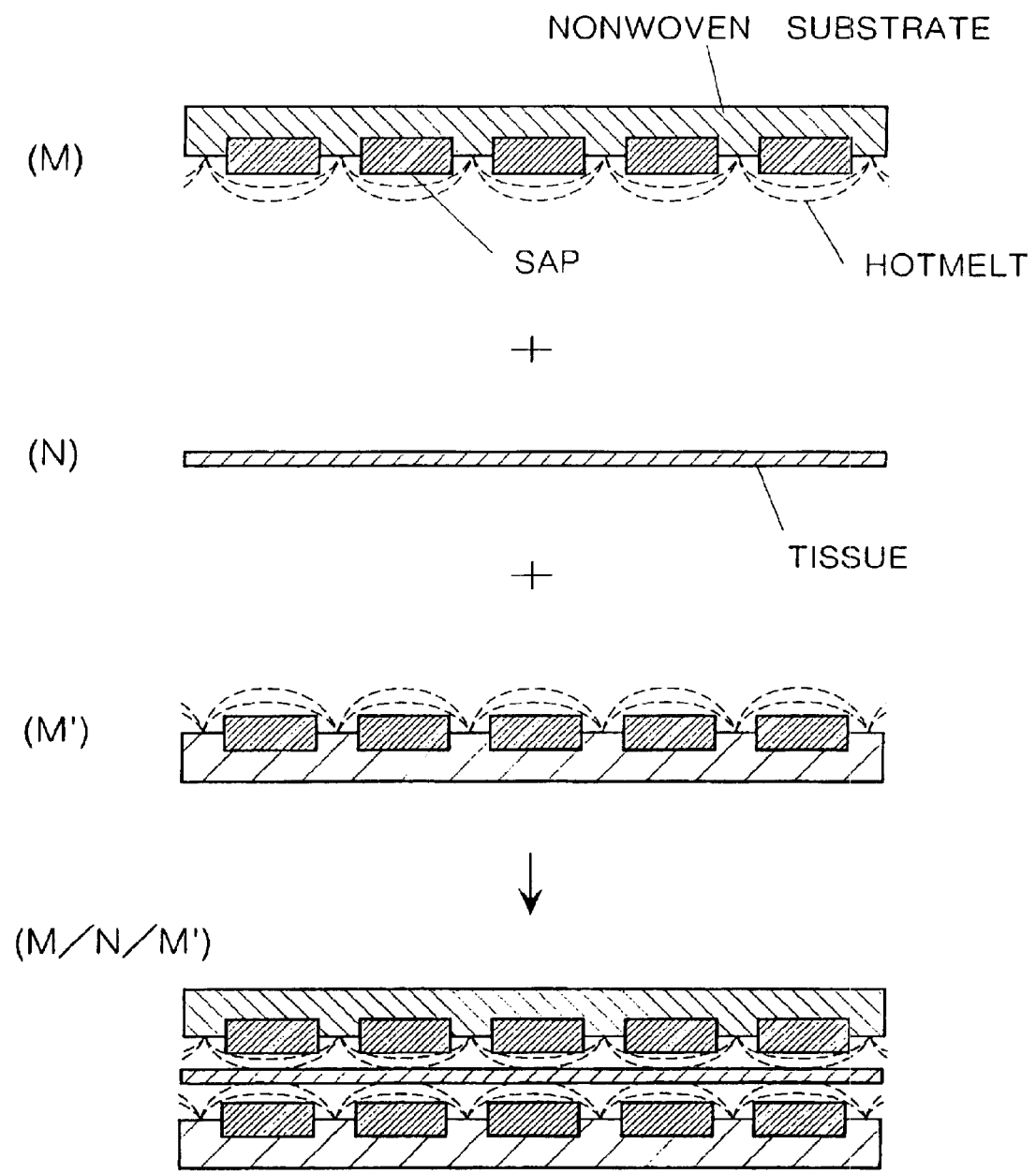
FIG. 18 shows the steps of manufacturing a still further modification of the highly absorbent composite sheet embodying the present invention.

As a second modification of the present invention, composite absorbents of which surface has been treated with hot-melt adhesive are integrally bonded with each other on their surfaces where the hot-melt and SAP are existent so that a composite absorbent of more SAP contained and improved in performance can be obtained. That is to say, as shown in FIG. 17, by integrating a composite absorbent as a first layer (M) and a composite absorbent as a second layer (M') by utilizing hot-melt existent on their surfaces through heating, adhering and compressing, a highly absorbent composite having a structure of (M/M') can be obtained. The SAP and nonwoven fabric constituting (M) and (M') can be the same or different in terms of properties. Furthermore, as shown in FIG. 18, the structure of a resultant absorbent composite can be made (M/N/M') by having a diffusion sheet or tissue (N) in between in integrating a first layer of a composite absorbent (M) and a second layer of a composite absorbent (M').

1. Preparation of Samples

1) Sizes of Samples

As a basic size, a sample was cut into 10 cm×80 cm.

The width was made as a repetition unit of a pattern depending on the kinds of samples. The width was approximately 10 to 30 cm.

2) Predrying

In order to maintain constant the water content during the evaluation, the predrying was conducted until the water content became 10% by weight or lower. In order to prevent deterioration of samples, however, the drying temperature was kept at 60° C. or lower.

3) Seasoning

The samples were allowed to stand for at least 12 hours at such temperature and humidity as make the water content 10% by weight. The coated surface of a sample was left exposed in constant temperature and humidity room or chamber.

2. Evaluation of Fixation of SAP Particles by Tester

1) Measuring of Weights of Samples (An Electronic Balance of 1 mg Sensitivity was used.).

The amount of SAP coated on a sample was calculated by deducting the weight of a substrate from the weight of a sample ($W_0$).

Figure 12D:
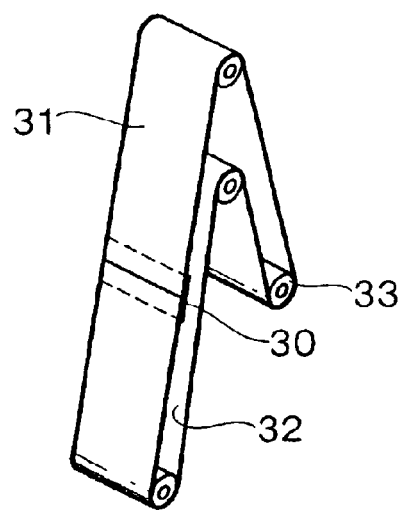
FIG. 12d is an oblique perspective view of the samples shown in FIG. 12c.

2) A Sample was Placed on the Above-mentioned Tester. With the Coated Surface Outside, the Substrate Surfaces of Both Ends of the Sample Were Linked by Means of Adhesive Tape 30 (FIG. 12d).

3) Load was Applied to the Sample by Using a Tension Roller. The Load Applied was 1 kg/10 cm Width.

4) Starting

In order to collect SAP particles as peeling or coming off, a black sheet of paper was placed beforehand under the place where the sample ran and then tester was started with the motor switched on. The running speed of the sample was set at 30 m/min.

5) Investigation of the Amount of SAP Particles Dropping Off During One Minute After Running The amount of SAP particles coming off as the amount of SAP particles insufficient in fixation (A zone) is checked during one minute of running after starting.

Figure 13:
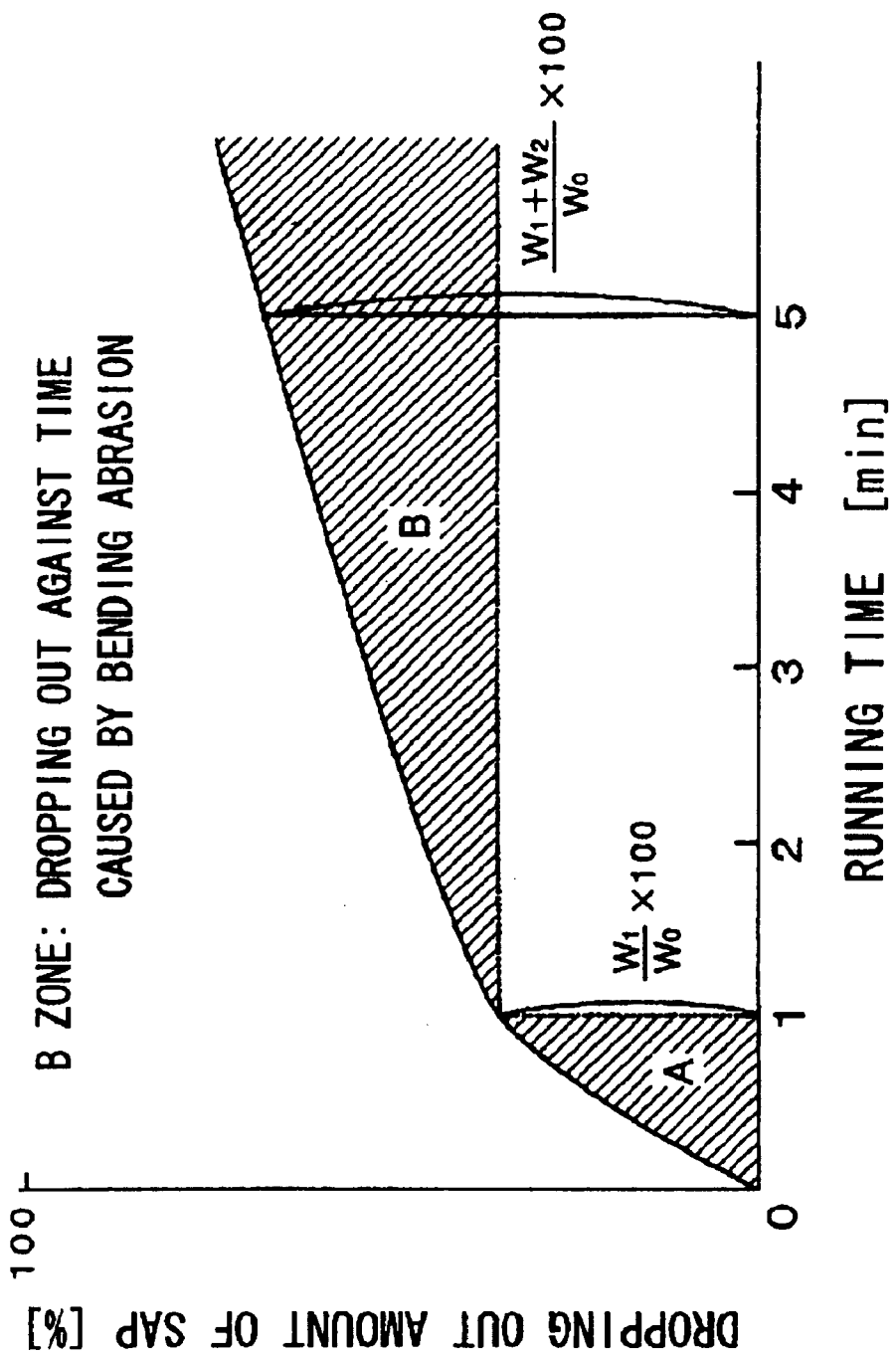
FIG. 13 is a graph showing the relation between the running time of a sample and the amount of the sample as come off.
Figure 14A:
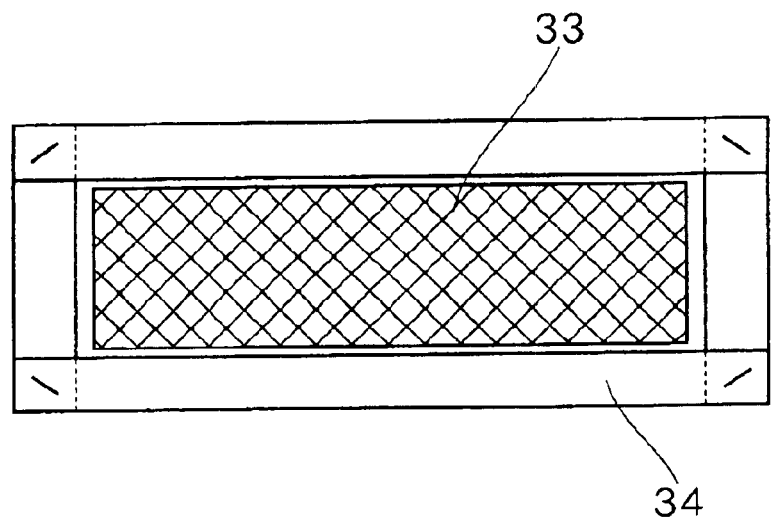
FIG. 14a is a plan view of an unit for evaluation of an absorbent as assembled.
Figure 14B:
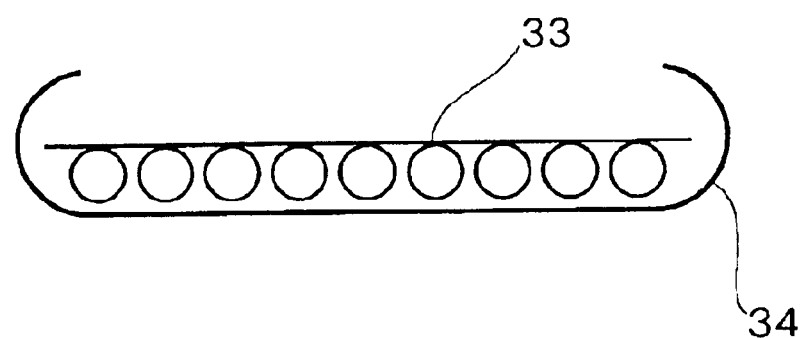

FIG. 13 is a graph showing the relation between the running time and the dropping out amount of SAP particles.

As the amount of SAP particles insufficient in fixation, the amount of SAP particles dropping out is checked during one minute of running after starting ($W_1$).

6) Investigation of the Amount of SAP Particles Dropping Out During Four Minutes After Restarting As the amount of SAP particles dropping out against time caused by bending abrasion (B zone) the amount of SAP particles dropping out during four minutes after restarting is checked ($W_2$).

7) Calculation of the Amount of SAP Particles Dropping Out

The amount dropping out during one minute after starting (amount of SAP particles insufficient in fixation)

=($W_1/W_0$)×100

The amount dropping out during five minutes after starting (total amount of SAP particles dropping out during five minutes after starting)

=[($W_1+W_2$)/$W_0$]×100

The examples of the present invention will be described.

EXAMPLE 1

Preparation of Composite Sheet

In the procedure described below a SAP composite sheet provided with a SAP layer for conducting a surface treatment with a hot-melt adhesive was prepared.

Preparation of Bulky Non-woven Substrate

A fiber web was prepared by folding a 20 g/m$^2$ carded web (P layer) of viscose rayon (1.5×42 mm), 30 g/m$^2$ carded web (Q layer) of PET fiber (6d×51 mm), and a sheet of tissue (R layer) of 20 g/m$^2$ N pulp in the order of P layer, Q layer and R layer and then by needling from the R layer side. In this fiber web fibers are entangled between the P layer and the Q layer and fibers of the R layer are mixed in the Q layer. The apparent specific gravity was 0.07 and it was in the form of bulky non-woven fabric.

Making Composite by Adding SAP

SAP in the form of flake (manufactured by Sanyo Chemical Co., Ltd. under the trademark Sunwet IM-500) was used. The SAP was uniformly added while a substrate was vibrated on a vibration plate so that the weight of SAP onto the R layer of said fiber web was 200 g/m$^2$. After making the SAP particles contained by the web and spraying water so that the content of SAP was 30 to 40% by weight, the web was compressed and stabilized to a blank sample 1.

Surface Treatment with Hot-melt Made into Fibers

<Hot-melt Applicator >

A curtain coat type applicator as shown in FIG. 6 (manufactured by Sun Tool Co., Ltd.) was used. Hot-melt adhesive of ethylene-vinyl acetate copolymer (hereinafter called "EVA") was applied in the amount of 1 g/m$^2$ onto the surface of said composite sheet that was to be treated. A composite sheet sample 2 having a structure as shown in FIG. 7a before the hot-melt treatment and a structure as shown in FIG. 7b after the hot-melt treatment.

<Hot-melt Adhesive Used >

The hot-melt adhesive used was Moresco Melt S-1396 D manufactured by Matsumura Oil Co., Ltd., whose main component was EVA. The properties of the hot-melt adhesive were as shown in Table 1 to follow. Little or no tacking problem was seen with the hot-melt adhesive.

TABLE 1

| Main Component | Content of Vinyl Acetate | MFR | Softening Point | Melt Viscosity (mPa · S) |
|---|---|---|---|---|
| E V A | 29.5~34.5 wt % | 60 ± 11 | 85° C. | 180° C. 11,000 |
| | | | | 160° C. 22,000 |
| | | | | 140° C. 48,000 |

Evaluation of Properties

The composite as obtained in the above-described procedure was evaluated in the above-described procedure. Table 2 to follow shows the measurements of stability in dry condition and holding in wet condition. From the results, it was proved that the covering effects with hot-melt adhesive were very outstanding.

TABLE 2

| | Stability of SAP in Dry Condition | | | |
|---|---|---|---|---|
| | Dropped Amount | Dropped Amount | Stability of SAP in Wet Condition | |
| Sample No. | after Treatment for 1 min (%) | after Treatment for 5 min (%) | Liquid Absorption Ratio (g/g) | Proportion of Fixed Part (%) |
| Example 1 | | | | |
| Blank Sample No. 1 | 3.1 | 5.7 | 42.0 | 0 |
| Working Sample No. 2 | 0.19 | 0.25 | 40.5 | 45.0 |
| Example 2 | | | | |
| Blank Sample No. 3 | 0.11 | 0.16 | 43.0 | 17.5 |
| Blank Sample No. 4 | 0.03 | 0.04 | 45.0 | 55.0 |
| Working Sample No. 5 | 0.01 | 0.02 | 41.0 | 79.0 |
| Working Sample No. 6 | 0 | 0.01 | 38.5 | 80.6 |

EXAMPLE 2

Preparation of Composite Sheet

SAP composite sheet provided with a SAP layer on which the surface treatment with hot-melt adhesive is applied was prepared in the following procedure:

Preparation of Bulky Non-woven Substrate

A dry spun lace non-woven fabric was obtained by blowing high pressure water stream to entangle a carded web of 35 g/m$^2$ consisting of 50% by weight of viscose rayon fiber (1.5 d×42 mm) and 50% by weight of PE/PET sheath/core bicomponent fiber (3 d)×51 mm). Said spun lace non-woven fabric was treated by means of an apparatus provided with a heating roll and a cooling roll as shown in FIG. 3. The non-woven fabric whose thickness was 2.5 mm and apparent specific gravity was 0.03 g/cm$^3$ in case of the load being 0.1 g/m$^2$ was obtained.

Making Composite by Adding SAP

An MFC dispersion liquid in which the concentration of MFC was 0.8% by weight and the ratio of ethanol/water was 70/30 (weight ratio) was prepared by diluting a 4% by weight water dispersion gel of MFC (S-MFC)(manufactured by ikushu Paper Mfg. Co., Ltd.) with ethanol with particulate SAP (manufactured by Mitsubishi Chemical Co., Ltd. under the trademark "Aquapearl 211 D") used. Note that the water retention of S-MFC used was 300%.

A co-dispersion slurry of SAP and MFC in which the content of SAP was 25% by weight was prepared by dispersing said SAP in this dispersion liquid. Said co-dispersion slurry as agitated was applied onto the surface of said non-woven fabric by means of a coater for thin layer chromatography. The resultant coated sheet was air dried, and dried by ironing after the remaining solvent was removed so that a blank sample of a composite sheet was obtained. The content of SAP in said composite was 200 $g/m^2$.

Surface Treatment with Hot-melt Made Into Fibers

With a curtain coat applicator (manufactured by Sun Tool Co.,Ltd.) as used in Example 1 and hot-melt adhesive (Matsumura Oil Co., Ltd.) as also used in Example 1 applied, the surface of the composite which was to be treated with SAP was covered by the hot-melt adhesive at the levels of 1 g/ $m^2$, 2 g/m2, and 5 $g/m^2$.

The conditions of the hot-melt adhesive made into fibers and the resultant network are as shown in FIGS. 8 A-1, 8 B-1 and 8 C-1, respectively. Also, the conditions of the surface of SAP being coated and covered are as shown in FIGS. 8 A-2 (Sample 4), 8 B-2 (Sample 5) and 8 C-2 (Sample 6).

Evaluation of Properties

Said composite as obtained in said procedure was evaluated. Table 2 shows the stability of SAP in dry condition and the holding of SAP in wet condition. Samples 4, 5 and 6 were much improved in surface stability in dry condition compared with the blank sample 3 and in addition, the fixation indicating the holding of SAP in wet condition was much improved.

EXAMPLE 3

Preparation of Non-woven substrate

A non-woven substrate of a dual structure as obtained by treating with a high pressure water stream a two layer web of a carded web of polyester fiber (6 d×51 mm) as the upper layer and of a carded web of viscose rayon fiber (1.5 d×38 mm) as the lower layer. The upper layer was bulky and the lower layer was of relatively high density and of average apparent specific gravity of 0.06 $g/cm^3$.

Preparation of Highly Absorbent Sheet

A water/ethanol dispersion liquid (the weight ratio of water/ethanol being 60/40) was prepared in which the concentration of MFC was 0.67% by adding water and ethanol to 2.5% aqueous solution of MFC (S-MFC Super microfibril cellulose) (manufactured by Tokushu Paper Mfg. Co., Ltd.). By adding to this dispersion liquid particulate SAP whose average particle size was 200 μm (manufactured by Mitsubishi Chemical Co., Ltd. under the trademark "Aquapearl AP-211D"), a slurry in which the content of SAP was 25% by weight. The slurry was applied by means of a coater onto the bulky upper layer surface composed by polyester fiber of said non-woven substrate of a dual structure so that striped line coats with coated portions of 7 mm width and uncoated portions of 3 mm width was obtained and a highly absorbent sheet coated with an average amount of SAP being 200 $g/m^2$.

Surface Treatment with Hot-melt Layer

The SAP coated surface of said highly absorbent sheet was surface treated by adding hot-melt material of E.V.A. type (manufactured by Matsumura Oil Co., Ltd. under the trademark "Morescomelt S-1396D") by means of a curtain spray method both in the first stage and the second stage with the amount of the hot-melt material added varied. The amount of the hot-melt material added was 0.5 $g/m^2$ in the first stage and 1.0 $g/m^2$ in the second stage as combined so that three samples 1, 2 and 3 were prepared. Also, a comparative sample which was treated only in one stage with the added amount of 3 $g/m^2$ was prepared to compare with those samples treated in two stages. Note that a main composition of the hot-melt material used in this Example was as follows:

| | |
|---|---|
| E. V. A. | 45% |
| Wax | 5% |
| Tackifire | 50% |

Evaluation Results of Stability

Figure 15:
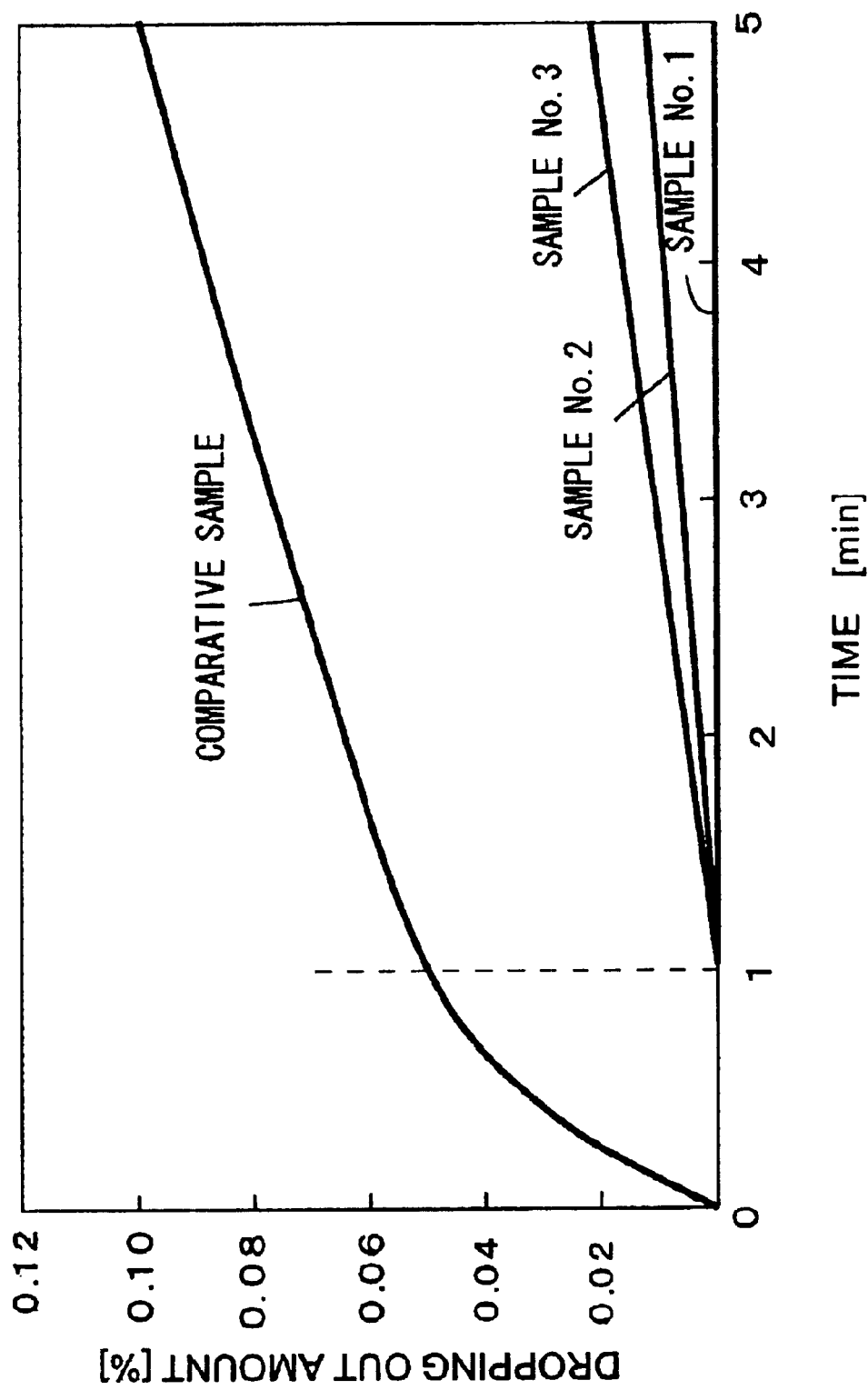
FIG. 15 is a graph showing obtained by plotting the change of SAP particles as come off as against time.

The stability in dry condition and the stability in absorbed condition of the highly absorbent sheets the surface of which was treated in the first and the second stage as mentioned above were evaluated. As for the stability in dry condition, the amount of SAP dropping out in percentage (%) was measured against time using an apparatus shown in FIGS. 12a to 12d and the measurements were plotted in FIG. 15 to indicate the change of dropping out amount in percentage against time. Also, the values during one minute and five minutes after initiation were indicated. The stability in wet (absorbed) condition was given in terms of the holding rate (%). The results are shown in Table 3 to follow:

TABLE 3

| | Condition of Hot-melt Surface Treatment | | Evaluation of Stability | | |
|---|---|---|---|---|---|
| | 1st Stage Treatment | 2nd Stage Treatment | Rate of Dropping Out in Dry Condition (%) | | Retention Stability After |
| Sample No. | (Curtain Spray) | (Curtain Spray) | After 1 min. | After 5 min. | Absorption (%) |
| Sample No. 1 | 0.5 $g/m^2$ | 0.5 $g/m^2$ | 0 | 0 | 80 |
| Sample No. 2 | 0.5 $g/m^2$ | 1.0 $g/m^2$ | 0 | 0.01 | 90 |
| Sample No. 3 | 1.0 $g/m^2$ | 1.0 $g/m^2$ | 0 | 0.02 | 95 |
| Comparative Sample | 3.0 $g/m^2$ | — | 0.05 | 0.10 | 50 |

In terms of the stability in dry condition, the samples which were treated in two stages gave better results compared with the samples which were treated in one stage only. It is shown that the sample treated in the combination of 0.5 $g/m^2$ in the first stage and 0.5 $g/m^2$ in the second stage gave the best results. The sample treated in one stage only with the amount of 3 $g/m^2$ applied was the worst of all. This indicates that a network of so fine and dense mesh as to hold even fine particles of SAP is much more important for the stability in dry condition and that in case of 3 $g/m^2$ the network of coarse and loose mesh is provided so that SAP particles may relatively drop out.

In terms of the stability in wet condition, too, any of the samples treated in two stages was better in the rate of holding than those treated in one stage only even though the added amount of the hot-melt material was less in the former samples and specifically, the sample treated with 1 $g/m^2$ in the first stage and 1 $g/m^2$ in the second stage gave the best results. This indicates that since the size of SAP particles gets larger as wet and swollen, the coarseness of fibers constituting the fibrous network has much to do with the stability after water is absorbed in the sense that coarse fibers do more hardly break than fibers constituting a network of fine and dense structure when swollen.

EXAMPLE 4

Preparation of Non-woven Substrate

Viscose cellulose non-woven fabric of 40 g/m$^2$ weight and 0.14 g/cm$^3$ apparent specific gravity (manufactured by Futamura Chemical Co., Ltd. under the trademark "TCF 404") was used to prepare a substrate.

Preparation of Highly Absorbent Sheet

Onto the surface of said substrate a slurry of SAP (manufactured by Mitsubishi Chemical Co., Ltd. under the trademark "Aquapearl 211 D"), a dispersion liquid in which SAP was 20% and S-MFC was 0.6% with the weight ratio of ethanol/water being 70/30 was applied by means of a coater in such way that a striped line coat with the coated portions of 10 mm width and the uncoated portions of 5 mm width was realized. Thus, a highly absorbent sheet with the coated amount of SAP being 150 g/m$^2$ was prepared.

Surface Treatment with Hot-melt Layers

In this Example a viscose cellulose substrate was used. Since the bonding of a viscose cellulose substrate with E.V.A. cannot be said to be good, hot-melt material (Morescomelt ME-125) in which polypropylene (P. P.) which is relatively easy to bond with cellulose although sticky was incorporated was used in the first stage. In the second stage Morescomelt S containing E.V.A. as a main component was used like in Example 3 above. Main components of Morescomelt ME-125 are as follows:

| | |
|---|---|
| E.V.A. | 48 parts |
| Tackyfire | 40 parts |
| P.P. | 12 parts |

The first stage aimed at anchoring effects for improving the affinity to the substrate and at making coarse and loose hot-melt treatment so that hot-melt material was added in lines of 7 mm intervals. Care was so taken that to the uncoated portions hot-melt material was added.

The second stage aimed at covering with fine and dense network and sample 4 was obtained by a curtain spray treatment.

Evaluation of Stability

In order to compare the effects of combining the first and the second stage, comparative samples, i.e. a comparative sample given a linear treatment only in the first stage and a comparative. sample given a curtain spray treatment only in the second stage were added. The results of evaluation are given in Table 4 to follow:

TABLE 4

| | Condition of Hot-melt Surface Treatment | | Evaluation of Stability | | |
|---|---|---|---|---|---|
| | 1st Stage Treatment | 2nd Stage Treatment | Rate of Dropping Out in Dry Condition (%) | | Retention Stability After |
| Sample No. | (Line Cost) | (Curtain Spray) | After 1 min. | After 5 min. | Absorption (%) |
| Sample No. 4 | 1.0 g/m$^2$ | 1.0 g/m$^2$ | 0.01 | 0.02 | 90 |
| Comparative Sample No. 1 | 2.0 g/m$^2$ | — | 0.50 | 2.0 | 5 or less |
| Comparative Sample No. 2 | — | 2.0 g/m$^2$ | 0.20 | 1.0 | 10 or less |

In case a linear treatment only is applied, it is not surprising that since the majority of SAP particles are not covered by hot-melt layer, the tendency of SAP particles dropping out in dry condition and the holding of SAP particles in wet and swollen condition are both extremely bad.

In case a curtain spray treatment alone is applied, too, the tendency of SAP particles dropping out and the holding of SAP particles are worse than anticipated. This may be because, even if the network is of fine and dense mesh, the affinity of the hot-melt layer to the cellulose fiber is bad and as such the boding between the two is accordingly bad, so that a part of the hot-melt layer may have left the area where it contacts with the substrate as absorbing moisture and thus getting swollen.

On the other hand, if the hot-melt layers in the first and the second stage are combined as in this Example, the linear hot-melt layer in the first stage serves as the anchor and thus the hot-melt layer is stably bonded with the hot-melt layer of the second stage so that the tendency of SAP particles dropping out in dry condition and the holding of SAP particles in wet and thus swollen condition are excellent.

EXAMPLE 5

Preparation of Non-woven Substrate

A non-woven raised fabric was prepared by folding, as bonded by needle punching method, a 40 g/m$^2$ web obtained by uniformly mixing polyester fiber (5 d×65 mm) and a sheath-core bicomponent fiber (3 d×41 mm) of polyethylene and polyester fibers in 50/50 ratio onto a 50 g/m$^2$ viscose rayon butter muslin fabric (net-like fabric). The weight of the non-woven fabric was 80 g/m$^2$ and the apparent specific gravity was 0.1 g/cm$^3$. Thus, it was very bulky.

Preparation of Highly Absorbent Sheet

Two types of SAP particles to be contained and held in a substrate were prepared. As SAP-l, particulate SAP of average particle diameter of 200 μm (manufactured by Mitsubishi Chemical Co., Ltd. under the trademark "Aquapearl 211D" and as SAP-2, flake-form SAP of average particle diameter of 400 μm (manufactured by Sanyo Chemical Co., Ltd. under the trademark "SunwetIM-5000") were used.

SAP-1 was added in the amount of 150 g/m$^2$ as uniformly as possible to said substrate as it was vibrated on a vibration plate, and then SAP-2 was added in the amount of 200 g/m$^2$ as placed on the SAP-1 so that a highly absorbent sheet was prepared which contained and held 350 g/m$^2$ of SAP. A majority of the SAP particles were embedded in the raised web, but when the surface of the web which held SAP particles faced downward, almost all of the SAP particles dropped out of the web. When the web was immersed in physiological salt water to evaluate the stability in wet and swollen condition, almost all of the SAP particles dropped out of the web shortly after the web started to swell so that the sample could not be used for the measurements. Thus, the sample was made a comparative sample.

Surface Treatment with Hot-melt Material

To the SAP coated surface of said highly absorbent sheet a hot-melt material of E.V.A. ("Morescomelt S13960") just like the one used in Example 3 above was applied by means of curtain spray type hot-melt adding apparatus in two stages to make sample 5.

For the sake of comparison, a comparative sample 4 for which the first stage treatment (curtain spray method) only was applied was prepared and tested in the same manner as the sample 5.

The stability tests identical with those conducted in Example 3 were conducted for the sample 5 and the comparative samples 3 and 4 and the results are shown in Table 5 to follow:

TABLE 5

| Sample No. | Condition of Hot-melt Surface Treatment | | Evaluation of Stability | | |
|---|---|---|---|---|---|
| | 1st Stage Treatment | 2nd Stage Treatment | Rate of Dropping Out in Dry Condition (%) | | Retention Stability After |
| | (Line Cost) | (Curtain Spray) | After 1 min. | After 5 min. | Absorption (%) |
| Sample No. 5 | 1.0 g/m² | 1.0 g/m² | 0 | 0.02 | 90 |
| Comparative Sample No. 3 | — | — | Cannot be measured | Cannot be measured | Cannot be measured |
| Comparative Sample No. 4 | 3.0 g/m² | — | 0.01 | 0.02 | 60 |

EXAMPLE 6

Preparation of Non-woven Substrate

A non-woven fabric obtained by applying a high pressure water stream to a carded web consisting of 60% polyester fiber (3 d×51 mm) and 40% viscose rayon fiber (1.5 d×35 mm ) as mixed was prepared as a substrate. The apparent specific gravity of the non-woven fabric was 0.08 g/cm³.

Preparation of Highly Water Absorbent Sheet

Solution A was prepared by adding 57.3 parts by weight of 48.5% by weight sodium hydroxide aqueous solution, 6.4 parts by weight of water, 0.15 part by weight of cross-linking agent (N, N'-methylene bis-acrylamide), and 5.0 parts by weight of 30% by weight hydrogen peroxide aqueous solution as oxidant to 125 parts by weight of 80% by weight acrylic acid aqueous solution. The monomer concentration of solution A was 60% by weight and its degree of neutralization was 50 mol %.

Separately, solution B was prepared by adding 57.3 parts by weight of 48.5% by weight sodium hydroxide aqueous solution, 9.9 parts by weight of water, 0.15 part by weight of cross-linking agent (N, N'-methylene bis-acrylamide) and 1.5 parts by weight of L-ascorbic acid as reducing agent to 125 parts by weight of 80% by weight acrylic acid aqueous solution. The monomer concentration and the degree of neutralization of solution B were the same as those of solution A.

Two nozzles of inside diameter of 0.13 mm each (manufactured by Ikeuchi Co., Ltd.) were used. With the angle made by the nozzles being 30 degrees and the distance between the nozzles being 4 mm, said solution A and said solution B heated to 40° C. were charged from one and the other nozzle at the same speed of 5 m/sec.

Solution A and solution B were merged just after coming out of the nozzles to form a liquid column of approximately 10 mm, and then the liquid was made to fall into ascending air current of 60° C. in droplets. These droplets were received by said non-woven substrate placed 100 cm below the tips of the nozzles, saturated steam vapor of 120° C. was blown out for 10 seconds to steam the substrate, and then, it was dried to the level of 10% of moisture content so that a highly absorbent sheet with 220 g/m² of SAP particles held and contained was obtained.

Surface Treatment with Hot-melt Material

Onto the side of the highly absorbent sheet which held and contained SAP particles, hot-melt material of E.V.A. type (Morescomelt S) was sprayed in 0.5 g/m² by means of curtain spray type hot-melt adding apparatus (manufactured by Sun Tool Co., Ltd.), in the first stage and then in the second stage the same hot-melt material was applied in 2 g/m² by means of spiral coat type hot-melt adding apparatus (manufactured by Sun Tool Co., Ltd.).

The resultant hot-melt treated highly absorbent composite sheet had a surface structure as shown in FIG. 11 as observed by electronic microscope. The sheet did not have any dust and powder splashing in dry test conditions and showed the retention of SAP particles at 85% or higher after absorbing and getting swollen.

EXAMPLE 7

Preparation of Composite Absorbent (M) whose Surface has been Treated with Hot-melt Adhesive Viscose rayon nonwoven fabric (1.5 d, 30 g/m²) (manufactured by Daiwabo Co., Ltd.) was prepared as a substrate.

SAP (trade name "AP50X" manufactured by Mitsubishi Chemical Co., Ltd.) was added in lines of approximately 8 mm width at approximately 3 mm intervals onto the substrate from a multi-tube type SAP feeder provided with a vibrator. A hot-melt adhesive (trade name "Moresco TN-288) having room temperature stickiness was added as fed from said curtain spray device in an amount to give 5 g/m² so as to cover the SAP from above the SAP in lines and the resultant material was then compressed on a cooling silicone roll so that a composite absorbent having a structure corresponding to M in FIG. 18 was prepared. The weight of SAP was 150 g/m².

Preparation of Composite Absorbent (AM) whose Surface has been Treated with Hot-melt Adhesive A bulky nonwoven fabric made by needle punching in a low density of 50 g/m² (manufactured by Ibyobo Co., Ltd.) was prepared as a substrate, as made of bicomponent hollow polyester fiber (8 d×51 mm) whose surface has been made hydrophilic.

SAP ("AP211D" manufactured by Mitsubishi Chemical Co., Ltd.) was added in lines of approximately 10 mm width at approximately 5 mm intervals onto the substrate from said multi-tube type SAP feeder. A hot-melt adhesive (Moresco TN-288) having room temperature stickiness was added as fed from said spiral type hot-melt applicator in an amount to give 10 g/m² so as to cover the SAP from above the SAP in lines and the resultant material was then compressed so that a composite absorbent having a structure corresponding to M' in FIG. 18 was prepared. The weight of SAP was 200 g/m².

Preparation of Wood Pulp Tissue (N)

Tissue available on the market of 30 g/m² was prepared to be used for wrapping an absorbent.

Preparation of Highly Absorbent Composite (M/N/M')

A highly absorbent composite having a structure of (M/N/M' was obtained by laminating the abovementioned M, M' and N in a way that N comes in between M and M' as shown in FIG. 18 and then compressing the same by means of a heated iron. The total weight of this highly absorbent composite was 475 g/m² and the content of SAP in it was 350 g/m². It was confirmed that the highly absorbent composite is an absorbent composite having both acquisition and diffusion properties.

What is claimed is:

1. Highly absorbent composite sheet comprising:
  a non-woven fabric substrate having a bulky structure;
  solid SAP partly contained inside said bulky structure and partly disposed on a surface of said non-woven substrate; and
  a fibrous network in a form of a mesh formed of a hot-melt adhesive as a thermally fusible component, said fibrous network contacting and covering said solid SAP to trap and hold the solid SAP so that said solid SAP is held in position.

2. The highly absorbent composite sheet of claim 1, further comprising fine cellulose disposed on the solid SAP as a layer, said fine cellulose being covered by the fibrous network.

3. The highly absorbent composite sheet of claim 1, wherein a coated amount of said hot-melt adhesive is 0.2 to 10 g/m².

4. The highly absorbent composite sheet of claim 1, wherein said hot-melt adhesive is mainly composed of ethylene-vinyl acetate copolymer and non-tacking.

5. The highly absorbent composite sheet of claim 4, wherein a content of vinyl acetate in ethylene-vinyl acetate which is a main composition of said hot-melt adhesive is 20 to 40% by weight and a thermal fluidity rate of said hot-melt adhesive is 50 to 150 g/10 minutes.

6. A highly absorbent composite comprising:
  a composite absorbent including a non-woven substrate, a SAP layer, and a fibrous network in a form of a mesh formed of a hot-melt adhesive layer as a thermally fusible component, said fibrous network contacting and substantially entirely covering said SAP layer to trap and hold the SAP layer, and
  a sheet material disposed on said adhesive layer and bonded with said composite absorbent by said hot-melt adhesive layer by an adhesive property thereof to form a composite structure.

7. A highly absorbent composite comprising:
  first and second composite absorbents, each comprising a non-woven substrate, an SAP layer, and a fibrous network in a form of a mesh formed of a hot-melt adhesive layer as a thermally fusible component, said fibrous network contacting and covering said SAP layer to trap and hold the SAP layer, said first composite absorbent being laid on the second composite absorbent such that said hot-melt adhesive layers contact with each other and are bonded together by an adhesive property thereof to form a two material composite structure.

8. The highly absorbent composite of claim 7, further comprising an additional sheet material interposed between said first and second composite absorbents and bonded thereto by the adhesive property of said hot-melt layers of said first and second composite absorbents to form a three material composite structure.

9. A highly absorbent composite sheet comprising:
  a non-woven substrate including a non-woven fabric with voids therein,
  solid SAP partly disposed in the voids and distributed almost all over in a layer on a surface of the non-woven fabric, and
  a dual fibrous network contacting and covering a surface of the solid SAP to trap and hold the solid SAP, said dual fibrous network having a first fibrous network in a form of dense mesh comprising a hot-melt adhesive as a thermally fusible component and a second fibrous network in a form of loose mesh coarser than the dense mesh and positioned over said first fibrous network.

10. The highly absorbent composite sheet of claim 9, wherein said dual fibrous network substantially entirely covers the solid SAP to thereby prevent the solid SAP from coming off.

11. The highly absorbent composite sheet of claim 9, wherein the fibers of said hot-melt layer of dense mesh are finer than the fibers of said hot-melt layer of loose mesh.

* * * * *